(12) United States Patent
John

(10) Patent No.: US 8,115,448 B2
(45) Date of Patent: Feb. 14, 2012

(54) SYSTEMS AND METHODS FOR WIRELESS POWER

(76) Inventor: Michael Sasha John, Larchmont, NY (US)

( * ) Notice: Subject to any disclaimer, the term of this patent is extended or adjusted under 35 U.S.C. 154(b) by 714 days.

(21) Appl. No.: 12/131,886

(22) Filed: Jun. 2, 2008

(65) Prior Publication Data

US 2009/0058361 A1 Mar. 5, 2009

Related U.S. Application Data

(60) Provisional application No. 60/977,086, filed on Oct. 2, 2007, provisional application No. 60/941,286, filed on Jun. 1, 2007, provisional application No. 60/941,287, filed on Jun. 1, 2007.

(51) Int. Cl.
*H01M 10/46* (2006.01)
(52) U.S. Cl. ...................................................... 320/108
(58) Field of Classification Search .................. 320/101, 320/103, 107, 108, 109, 116; 343/701, 703
See application file for complete search history.

(56) References Cited

U.S. PATENT DOCUMENTS

| | | | |
|---|---|---|---|
| 5,522,856 A | 6/1996 | Reineman |
| 5,697,956 A | 12/1997 | Bornzin |
| 5,957,956 A | 9/1999 | Kroll et al. |
| 6,067,473 A | 5/2000 | Greeninger |
| 6,108,579 A | 8/2000 | Snell |
| 6,127,799 A | 10/2000 | Krishnan |
| 6,664,770 B1 | 12/2003 | Bartels |
| 6,856,291 B2 | 2/2005 | Mickle et al. |
| 6,967,462 B1 | 11/2005 | Landis |
| 6,975,198 B2 | 12/2005 | Baarman et al. |
| 7,027,311 B2 | 4/2006 | Vanderelli et al. |
| 7,042,196 B2 | 5/2006 | Ka-Lai et al. |
| 7,084,605 B2 | 8/2006 | Mickle |
| 7,116,200 B2 | 10/2006 | Baarman et al. |
| 7,118,240 B2 | 10/2006 | Baarman et al. |
| 7,126,450 B2 | 10/2006 | Baarman et al. |
| 7,127,293 B2 | 10/2006 | MacDonald |
| 7,132,918 B2 | 11/2006 | Baarman et al. |
| 7,212,414 B2 | 5/2007 | Baarman |
| 7,251,527 B2 | 7/2007 | Lyden |
| 7,288,918 B2 | 10/2007 | DiStefano |
| 7,340,304 B2 | 3/2008 | MacDonald |
| 2003/0214255 A1 | 11/2003 | Baarman et al. |
| 2004/0130915 A1 | 7/2004 | Baarman et al. |
| 2004/0130916 A1 | 7/2004 | Baarman et al. |
| 2004/0142733 A1 | 7/2004 | Parise |
| 2004/0150934 A1 | 8/2004 | Baarman |
| 2004/0232845 A1 | 11/2004 | Baarman et al. |

(Continued)

FOREIGN PATENT DOCUMENTS

WO WO2007084717 7/2007

*Primary Examiner* — Edward Tso

(57) ABSTRACT

The present invention is a wireless power system which includes components which can be recharged by harvesting wireless power, wireless power transmitters for transmitting the power, and devices which are powered from the components. Features such as temperature monitoring, tiered network protocols including both data and power communication, and power management strategies related to both charging and non-charging operations, are used to improve performance of the wireless network. Rechargeable batteries which are configured to be recharged using wireless power have unique components specifically tailored for recharging operations rather than for providing power to a device. A wireless power supply for powering implanted devices benefits from an external patient controller which contains features for adjusting both power transmission and harvesting provided by other components of the wireless power network.

15 Claims, 19 Drawing Sheets

U.S. PATENT DOCUMENTS

| | | |
|---|---|---|
| 2005/0021134 A1 | 1/2005 | Opie |
| 2005/0033382 A1 | 2/2005 | Single |
| 2005/0104453 A1 | 5/2005 | Vanderelli et al. |
| 2005/0122058 A1 | 6/2005 | Baarman et al. |
| 2005/0122059 A1 | 6/2005 | Baarman et al. |
| 2005/0127849 A1 | 6/2005 | Baarman et al. |
| 2005/0127850 A1 | 6/2005 | Baarman et al. |
| 2005/0194926 A1 | 9/2005 | Di Stefano |
| 2006/0164866 A1 | 7/2006 | Vanderelli et al. |
| 2006/0199620 A1 | 9/2006 | Greene et al. |
| 2006/0205381 A1 | 9/2006 | Beart et al. |
| 2006/0238365 A1 | 10/2006 | Vecchione et al. |
| 2006/0270440 A1 | 11/2006 | Shearer et al. |
| 2006/0281435 A1 | 12/2006 | Shearer et al. |
| 2007/0010295 A1 | 1/2007 | Greene et al. |
| 2007/0021140 A1 | 1/2007 | Keyes, IV |
| 2007/0117596 A1 | 5/2007 | Greene et al. |
| 2007/0176840 A1 | 8/2007 | Pristas et al. |
| 2007/0178945 A1 | 8/2007 | Cook |
| 2008/0014897 A1 | 1/2008 | Cook et al. |
| 2008/0300660 A1* | 12/2008 | John ............................ 607/61 |

* cited by examiner

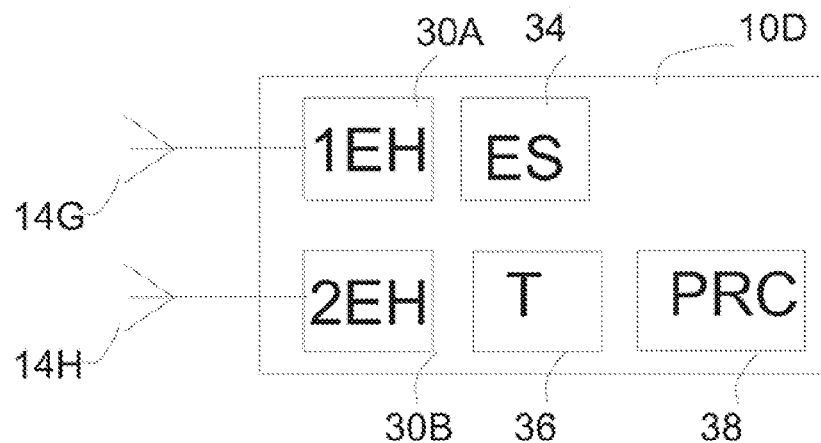
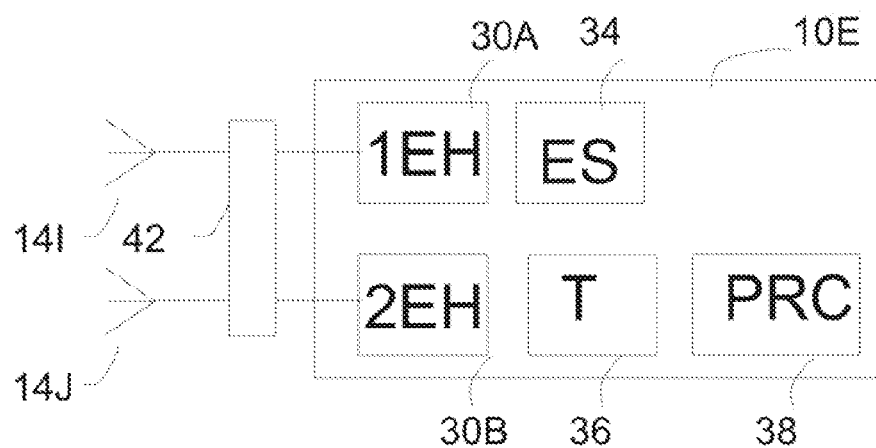

Half wave

Full wave
non-center
tapped

Full wave
center
tapped

SYSTEMS AND METHODS FOR WIRELESS POWER

This application claims priority to U.S. provisional application 60/977,086 filed on Oct. 2, 2007 entitled "Systems and Methods for Wireless Power", 60/941,286 filed on Jun. 1, 2007 entitled "Systems and Methods for Wireless Power", 60/941,287 field on Jun. 1, 2007 entitled "Power generation for implantable devices", and co-pending application not-yet-known filed on Jun. 1, 2008 entitled "Power generation for implantable devices", incorporated by reference herein.

BACKGROUND OF THE INVENTION

This invention is generally in the field of wireless power transmitters and receivers.

A number of technologies have recently evolved for providing wireless power according to various schemes. In U.S. Pat. No. 7,027,311, etc. systems and methods are described for wireless power systems and methods applicable to both near-field (i.e., induction) and mid-to-far-field transmission/reception of power. PowerCast (www.powercastco.com) provides a wireless receiver ('harvester') which is capable of converting RF energy which is either ambient due to, for example, remotely generated radio transmissions, or which can be actively transmitted by a PowerCast power transmitter. Technologies promoted by other companies (e.g. www.s-plashpower.com; www.wildcharge.com; www.ecoupled.com) rely primarily upon inductive coupling technologies, and may utilize an inductive pad (e.g. a 'Splashpad') which transmits power to receiver surfaces within the device that is to be powered. Another technology for transmitting energy over midrange distances (e.g., 9-20 feet or so) utilizes a non-radiative resonant energy transfer in which the transmitter and receiver are both tuned to the same MHz-range frequency through use of resonant beacons (e.g., Karalis, A, Joannopoulos, J. D. and Soljačić, M, Efficient wireless non-radiative mid-range energy transfer (2006), also see http://en.wikipedia.org/wiki/Wireless energy transfer for review). Many of the features of the current invention are relevant to providing advantages across these different modes of providing wireless power.

Wireless technologies using either induction or mid-/far-field transmission must often address issues such as identifying devices to be charged so that these can be charged according to protocols that address their needs and capacities. In the case of inductive coupling, relative orientation of transmission/reception surfaces of devices are especially important in order to ensure correct and efficient transmission of power without shorts, surges, or ineffective transmission/reception. Some recent advances have addressed these issues in order to create devices which are more user friendly and less prone to power-transfer failure. The currently existing eCoupled technology includes an inductively coupled power circuit that dynamically seeks resonance with receiving devices: the primary circuit is able to adapt its operation to match the characteristics of the load(s) receiving circuit. The power supply circuit automatically attempts to optimize efficiency by establishing resonance between the primary and secondary coils for any given load. Communication between the transmitter and individual receiving devices can occur in real time, which allows the technology to determine not only power needs but other power characteristics of the receiving device. For example factors such as age of a battery, number of charging lifecycles, time since last charge, resistance to certain temporal charge-patterns and other characteristics of power provided, can be established in order to realize improved power supply and efficiency. Resonance-seeking strategies also allow some freedom in positioning the secondary (i.e. harvesting/receiving) relative to the primary (transmitting) components of devices while maintaining efficient transmission of electrical power. Existing inductive technologies have thereby overcome a number of traditional limitations which have previously impeded wider reliance of inductive power, such as spatial rigidity, static loads and unacceptable power losses by adapting to various loads (e.g., both low- and high-power demands), and lack of user friendliness. Using these new schemes, energy transfer efficiency can be increased over conventional inductive coupling to result in power losses as low as 10%. This makes some wireless technologies comparable to hardwired connections in terms of energy costs. Much of the safety issues have also been overcome, allowing these new inductive technologies to come much closer to, and even surpass, safety issues that match conventional 'wired' charging methods.

Some related technologies for transmission and reception, which can be utilized by the current invention, have been filed by Powercast and include patent applications for example, US20070010295; US20060281435; US20060270440; US20060199620; US20060164866; US20050104453; US20070117596, entitled 'Radio-frequency (RF) power portal'; and U.S. Pat. No. 7,027,311, entitled 'Method and apparatus for a wireless power supply', which increases power reception by harvesting across a collection of frequencies.

Some related technologies filed by eCoupled include, for example, Inductive Coil Assembly (U.S. Pat. No. 6,975,198; U.S. Pat. No. 7,116,200; US 2004/0232845); Inductively Powered Apparatus (U.S. Pat. No. 7,118,240 B2; U.S. Pat. Nos. 7,126,450; 7,132,918; US 2003/0214255); Adaptive Inductive Power Supply with Communication (US 2004/0130915); Adaptive Inductive Power Supply (US 2004/0130916); Adapter (US 2004/0150934); Inductively Powered Apparatus (US 2005/0127850; US 2005/0127849; US 2005/0122059; US 2005/0122058. Splashpower has obtained U.S. patents such as U.S. Pat. No. 7,042,196.

Other relevant art includes, US20050194926 entitled, 'Wireless battery charger via carrier frequency signal'; U.S. Pat. No. 6,127,799, entitled 'Method and apparatus for wireless powering and recharging; U.S. Pat. No. 6,856,291 entitled 'Energy harvesting circuits and associated methods; 20060238365 entitled 'Short-range wireless power transmission and reception'; US20040142733 entitled 'Remote power recharge for electronic equipment'; U.S. Pat. No. 6,967,462 entitled 'Charging of devices by microwave power beaming'; U.S. Pat. No. 7,084,605, entitled 'Energy harvesting circuit'; U.S. Pat. No. 7,212,414 entitled 'Adaptive inductive power supply' and describes a power transmitter which automatically adjusts its power transmission based upon sensed resonance with power receivers which it may charge; US20079178945 entitled 'Method and system for powering and electric device via a wireless link', describes rectifier circuitry, which may include Germanium-based rectifiers as well as those based upon silicon, gallium arsenide, and other semiconductor materials, and further utilizes a pair of diodes to permit a rechargeable battery to be charged by either a wire charging unit or signals received by the receiving antenna; US2007176840 entitled 'Multi-receiver communication system with distributed aperture antenna', provides for an antenna with holes configured to produce low level local power fields; U.S. Pat. No. 6,664,770 entitled 'Wireless power transmission system with increased voltage output', is for increased power reception and provides a radio-signal shaped to allow the receiving circuitry to operate towards this purpose; US20060204381 entitled 'Adapting portable electrical devices to receive power wirelessly', describes solutions for universally incorporating wireless power into devices such as cellular phones without requiring buy-in from the original equipment manufacturer (OEM). The 'universal adapters' suggested therein must be configured to work with various unique devices rather than truly being universal. While this solution avoids efforts for the OEM, it also requires that these 'universal adapters' come in as many shapes and sizes as there are batteries for the devices; WO2007084717 entitled 'Method and apparatus for delivering energy to and electrical or electronic device via a wireless link', describes use of a directional antenna and tracking system for adjusting the direction of the beamed energy; and, US20070021140 entitled 'Wireless power transmission systems and methods' describes providing wireless data and power in a factory environment. All of these patents and patent applications are incorporated by reference herein and describe technologies which will be generally treated here as wireless power systems that relate to the invention including wireless power transmission and wireless power reception.

These new wireless power systems are still hindered by a number of issues. Most embodiments oblige manufacturers to incorporate the wireless harvesting technologies into their devices, requiring 'buy in' from large original equipment manufacturers (OEMs). Similar to the issues which have plagued utilization of compact discs, and cord adapters used by different devices, the standards, protocols, and features of wireless transmitting and receiving devices may vary greatly between companies. Systems and methods are needed for adapting wireless power technologies to 'open' rather than 'closed' platforms, allowing the adaptation of wireless power to occur without manufactures tying themselves and their product designs to particular wireless technologies, protocols, and the like. Further, when transmission of data and power are both provided in a wireless manner, the integrity of both types of transmission should be ensured, especially in the case of medical related applications. Additionally, recharging operations should interfere minimally with normal operations of devices that rely upon wireless power.

SUMMARY OF THE INVENTION

In one embodiment of the present invention system, a wireless power supply is provided which can be recharged by wireless power and does not require modification of devices within which the wireless power supply is used.

When the wireless power supply is realized in a 'wireless-battery' or 'wireless power-pack', this can be used with wireless power devices without requiring modification of the devices including the device circuitry, power storage compartments, software, displays, controls, operation or accessories.

When the wireless power supply is realized in a 'wireless-battery' or 'wireless power-pack', this can be used with wireless power devices in conjunction with modifications of the devices including the device circuitry, adapters for the power storage compartments, device software, displays, controls, operations and device accessories.

When the wireless power supply is realized in a 'wireless-power' battery, this battery can be realized with a set of re-charging contacts which are distinct from the traditional battery terminals, and are partially or solely used for recharging operations. Further the wireless power battery can be configured for communication with a wireless charging apparatus, for example, to communicate a signal reflective of power level or operational status.

The present invention system contains a wireless power supply, which can be recharged by wireless power and which adapts the transmission of power provided by a power transmitter to augment the power that is received and harvested.

The present invention system contains a wireless power supply which can be recharged by wireless power and which further uses conventional interface ports such as a USB port for transmission of power and data.

The present invention system contains a device having a wireless power supplier/transmitter which can be recharged by wireless power and which can also be configured for wire-based data communication.

The present invention system contains a wireless power supply which can be recharged by wireless power and which is configured to be used with conventional rechargeable batteries.

The present invention system contains a wireless power supply which can be recharged by wireless power and which also provides for de-charging and re-charging to occur as a maintenance operation and promote increased battery performance and lifespan.

The present invention system is a wireless power supply which can be recharged by wireless power and which also provides for parameter estimation, which can be used to alter charging operations, so that unwanted results are deterred, such as temperature parameters exceeding a selected range, said unwanted temperature range being related to charging or to discomfort of a patient, if the wireless power receiver is implanted in a patient.

The present invention system has a wireless power harvester and transmitter, each of which may be configured primarily for directional or non-directional antennae.

The present invention system comprises a wireless power system having components that are configured for monitoring or transmitting data and/or receiving data through AC powerlines.

The present invention system comprises a wireless data-power system in which the wireless data transmission operations; the wireless power transmission operations; and the interrupt requests issued by different components of the system are assigned priority based upon priority factors such as the type of information or operations which are occurring or which are scheduled to occur. The wireless transmission of data and power can include operation of a medical device, an implanted medical device, a patient controller, and instrumentation and tools used during surgery or within the emergency/intensive care unit of a hospital.

These and other preferred embodiments, objects and advantages of this invention will become obvious to a person of ordinary skill in this art upon reading of the detailed description of this invention including the associated drawings as presented herein.

BRIEF DESCRIPTION OF THE DRAWINGS

FIGS. 2A-2E illustrates alternative block diagrams of power harvesters configured to achieve different advantages.

DETAILED DESCRIPTION OF THE INVENTION

Figure 1A:
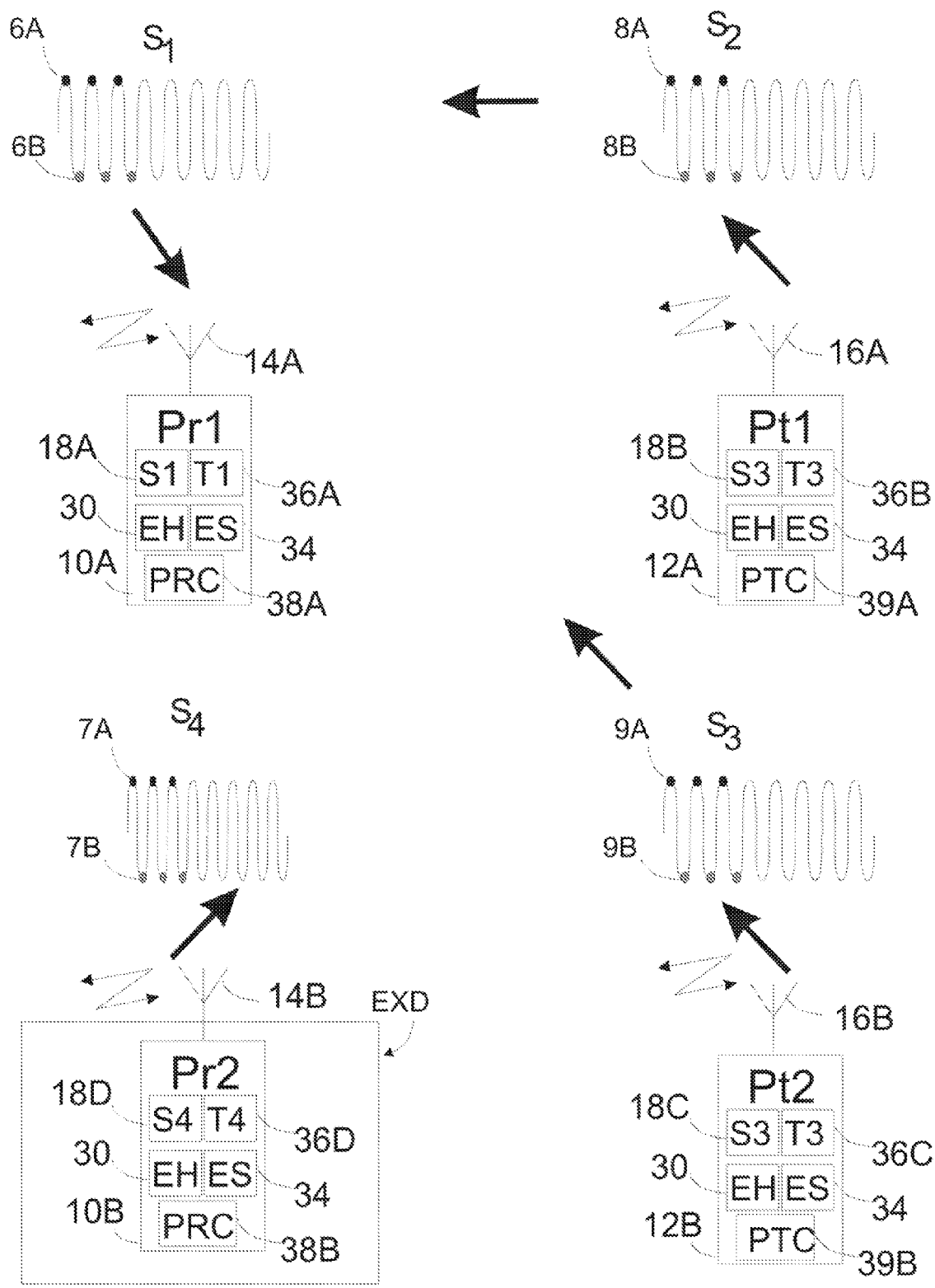
FIG. 1A illustrates a preferred wireless transmitter and receiver system configured for increasing powerless energy transfer, and is configured with a secondary receiver and secondary transmitter.
Figure 1B:
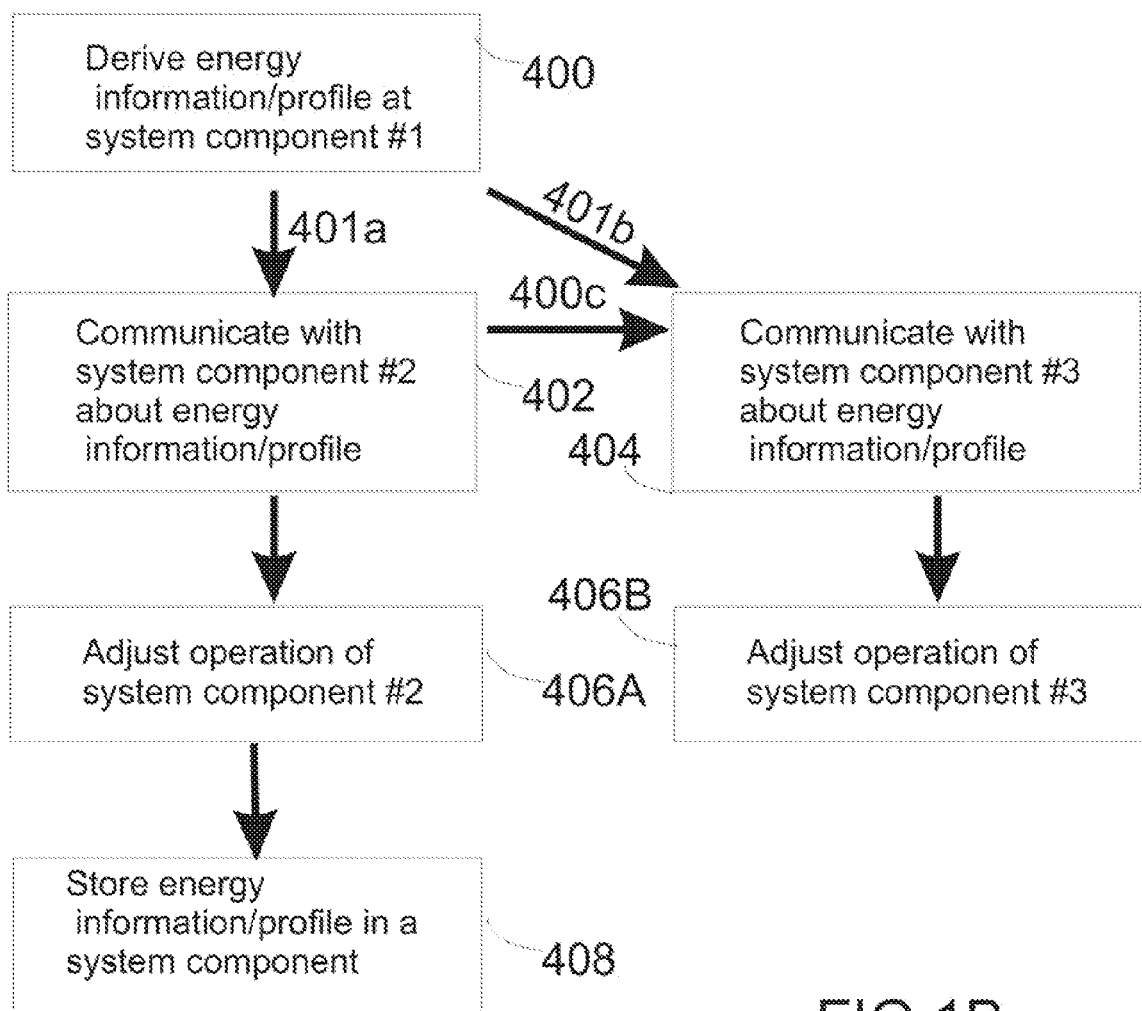
FIGS. 1B-1C illustrate preferred methods of using a wireless transmitter and receiver system.

Systems and Methods for Improving Wireless Power Provided in Wireless Power Systems FIG. 1A shows a first wireless power receiver (PR1) 10A and first wireless power transmitter (PT1) 12A which are configured with antennae 14A and 16A respectively. The PR1 10A and the PR1 12A can each contain sensor modules, 18A and 18B, respectively which are capable of deriving an energy profile. An energy profile comprises an estimation across a specified interval, of at least one characteristic of a signal related to wireless power, such as amplitudes, phases, or "spectral profile" of a wireless power signal. The PR1 10A is able to use its energy harvesting module 30 to harness wireless energy signals which exist in an ambient manner (S1) or energy signals which are transmitted by components of the wireless power system (S2) such as by the PT1 12A. The sensor module 18A of the PR1 10A can be configured to sense energy profiles and in particular a characteristic such as the phase of various types of ambient spectral energy (e.g. 70 Hz refresh rate of a computer display). The power receiver control module 38A of PR1 10A can then operate the transmission and communication module 36A to transmit this information to the PT1 12A (which receives this information using its transmission and communication module 36B), so that it may adjust the phase of the transmitted energy S2 which is subsequently provided in order to increase the probability that the two types of energy signals S1 and S2 add constructively rather than destructively in the location of the PR1 10A. This process is shown in the method of FIG. 1B in which step 400 occurs at PR1 10A (in this case system component #1) and the information is transmitted 402 to PT1 (component #2 in this example), which then adjusts its operation 406A such as the parameters of the energy to be transmitted. This strategy may also work when two or more energy transmitters (PT1 & PT2) are used in a wireless power system (via steps 404, and 406B). Alternatively, the power transmitter 12A can operate its energy profile sensor 18B to detect the spectral profile of ambient energy S1 (e.g. frequency, magnitude and phase characteristics) and adjust the characteristics of the transmitted energy S2 which it transmits in order to cause an intended summation of the phases of signals S1 and S2, especially with respect to the reception of energy by PR1 10A. Further the energy profile sensor 18B of the power transmitter 12A can monitor the mains line power signal either as that which is received by its antenna 16A or by monitoring the AC power which it receives directly from the wall socket which is normally powering the energy storage module 34B of the PT1 12A (this monitoring can assess the amplitude and phase of the AC power and can also detect command signals which may be transmitted over the power network as will be described further). In order to increase the environmental friendliness of the system, an AC/DC converter can be implemented within the energy harvesting module 30 or the energy storage module 34, or within another module of the device and can be shut off by the PTC 39 sot that the device operates in "power saving mode" when energy transmission is not occurring if the energy storage module 34 contains a rechargeable storage cell.

In some instances the energy which is locally transmitted (S2) may have a similar energy signature to energy which is ambient. Such an example is 50 or 60 Hz mains line energy, energy from other wireless power transmitters, energy from cordless phones, cellular or microwave transmitters, etc. Ambient energy strength may change depending upon location. For example, when a power receiver 10A is located outdoors then ambient RF energy S1, such as that transmitted by radio-towers, may be several orders of magnitude larger than mains-line energy, while when the PR1 10A is located indoors, the opposite situation can occur. The power transmitter 12 may transmit energy S2 using a carrier of 50 or 60 Hz energy, or may use a carrier of a much higher frequency and can modulate this energy at a slower rate such as at 50 or 60 Hz. In this case, there is a risk that transmitted energy signals S2 having energy (or rectified energy) at 50-60 Hz will be out of phase with the ambient 60 Hz energy signals S1, leading to destructive interference and a subsequent decrease in energy harvesting by the device 10A. In the best case, the peaks 6A of the ambient energy S1 will combine with the peaks 8A of the transmitted energy S2 (especially at the site of the harvesting antenna). Rather than 50 or 60 Hz energy, the ambient energy may be much faster, for example, in the Megahertz or Gigahertz range. Although the antenna required to receive power at 50 or 60 Hz may be relatively large, line energy is used in this example both because it is relatively common and also because fractal-based antennae may be sufficiently well designed that this energy is sufficient for harvesting by smaller scale antennae.

FIG. 1A further shows a first power receiver (PR1) 10A and a first power transmitter (PT1) 12A and a second power transmitter (PT2) 12B. The PT2 may transmit energy signals S3 which is preferred to realize a desired relationship with ambient energy signals S1, and transmitted energy signals S2. The desired relationship can be that S3 is will be approximately in-phase especially with respect to the reception of these signals at PR1 10A, or the parameters of S3 can be selected so that S3 uses a different band of energy than is supplied in S2, or other desired feature. The PR1 12A contains an antenna 16A, and an energy profile sensor 18B, and can sense the energy signal S3 profile in order to adjust a parameter (e.g., the phase or frequency range) of the energy signal it subsequently transmits as S2. Additionally, the PR1 10A can contain a sensor 18A which can compute energy profiles of at least one of S1, S2 and S3. If these are of the same frequency, these may be uniquely measured at independent times, during a calibration routine that is provided by a cooperation of the power receiver control 38A and at least one power transmitter control 39A, 39B of the first or second power transmitter device 12A, 12B. In this case the controls cause the implementation of a power calibration routine which can occur as per FIG. 1B, in which steps 400, 402, and 406A occur at time 1, and then 400, 400, 406B occur at time 2, so that the contribution of the power sent by each transmitted can be independently assessed by the PR1 10A. Obviously this strategy can be extended to the case where there are several receivers and transmitter in the wireless power network. The power transmitter control 39 can provide means for turning the power transmitter on and off both manually and due to wireless command signals.

Systems and Methods for Increasing Wireless Power Reception by Implanted Systems FIG. 1A further shows a first power receiver (PR1) 10A and a second power receiver (PR2) 10B and power transmitter (PT1) 12A. The second power receiver PR2 10B contains an antenna 14B, a sensor 18D, and a transmitter 36D. In one embodiment, the PR2 10B can be different than the PR1 10A in that its power receiver controller 38B can contain modules and algorithms that are used for assessing energy profiles associated with different power transmission schemes implemented by the transmitter PT1 12A. The power receiver controller 38B can also contain a memory which stores parameters (such as amounts of power received as can occur in step 408) for different harvesting operational settings that are implemented by the energy harvesting module 30. For example, the PR2 10B can coordinate its operation with the operation of the transmitter 12A and can assess how much power is obtained when the transmitter 12A transmits power signals S2 using different transmission strategies and transmitted power signals. Alternatively, the PR2 10B can measure ambient (and/or transmitted) energy signals and can alter the harvesting parameter values settings used by the energy harvesting module 30D, in order to attempt to improve harvesting of these energy signals (in a similar fashion to that done by modules 200, 214, 216 and 224 of FIG. 8A). Based upon these optimization tests (i.e. system calibration), the power harvesting settings used by the energy harvesting modules 30D and 30A (of PR1 and PR2), and/or transmission settings used by PT1 (and PT2) can be adjusted to improve performance. The PR2 can contain a power harvesting module 30D which provides power which can be stored or may only relay power signals to a sensor 18D that is part of a power energy profile module (as may occur if its energy storage module 34 is powered by other means, such as a battery or solar power). The use of a second power receiver device 10B, is beneficial in a number of applications such as when the first power receiver 10A is embodied within a device such as an implanted medical device. In this case, the optimization/calibration routines and communication between the power-receiver 10B and at least one power transmitter 12A can require ample power and circuitry, which may not be easily realizable by an implanted device. By configuring the system so that a second power receiver 10B is situated external to the patient (e.g. existing as part of an external device (EXD) which is a pager sized patient programmer), the power receiver 10a which resides within the patient is not required to utilize power, computational, or other resources that are related to optimization/calibration, and does not require a design incorporating the associated circuitry.

When the second power receiver 10B is implemented in an EXD, the EXD can be configured to assess the efficiency of different power transmission/reception configurations 410 (which may include communicating with a power transmitter 12A) and to select which configuration is best before transmitting this information to an implanted device 411B (if this is necessary) which relies upon power receiver 10A and to power transmitter 12A so that this configuration may be relied upon. The EXD can also be configured with a number of additional advantageous features such as those shown in modules of FIG. 8A. The EXD can measure the energy profile of energy harvested over time by power receiver 10B and to issue a patient alert signal 420 (via module 222) if the energy is not above a minimum selected level. The EXD can also enable the patient to provide patient input which is used for adjusting the operation of the first and second power receiver devices 10A, 10B, and power transmitter device 12A. For example, if the patient sees from a graphical display on the EXD that not much power is being received, then the patient may manually select another power-protocol which involves adjusting at least one of the transmission and harvesting. If a patient adjusts the power-protocol from 'protocol A' to 'protocol B' then this may require synchronizing operations of the power transmitter device 12A and the implanted power receiver device 10A (via communication steps 411*a* and 411*b*). Accordingly, the EXD can also operate the second power receiver device 10B to synchronize operations of the power transmitter device 12A and the implanted power receiver device 10A. Allowing the EXD to manage and control the timing and synchronized operation of the implanted device and the power transmitter can be based upon the operations of an implanted device powered by the first power receiver device, and may include the EXD controlling the other components of the system based upon scheduled events in the treatment regimen of the implanted device.

Figure 2A:
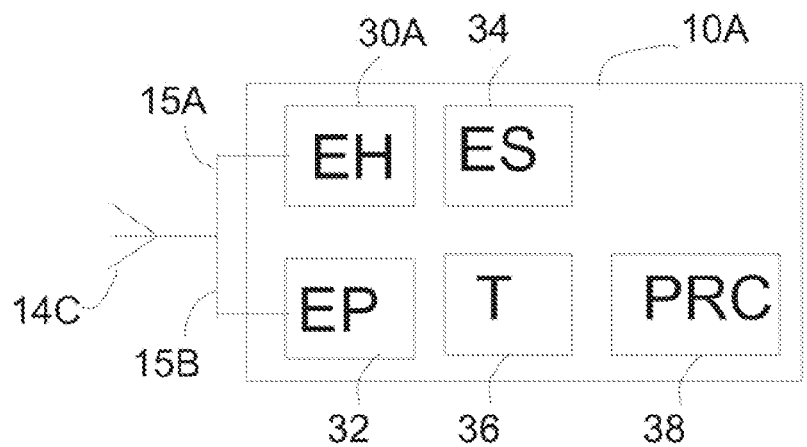

Systems and Methods for Optimizing Power Generation in Wireless Power Systems While the power receiver of FIG. 1A can be embodied in a number of manners (e.g. FIG. 8A), some preferred embodiments can utilize portions and combinations of any of the designs illustrated in FIGS. 2A-2E. FIG. 2A shows a wireless power receiver module 10A which contains an energy harvester module 30 configured for harvesting RF energy. An energy profile module 32 is configured for calculating, in a fixed or programmable manner, at least one of the following: current and historical energy profiles for selected spectral energy bands; current energy conversion rates; a history of energy conversion rates; profiles of different energies which are ambient in the local environment; and, profiles of at least one transmitted energy signal (transmitted by a component of the wireless system) having a selected frequency range. An energy storage module 34 can contain at least a first rechargeable battery or at least one capacitor and may also include a second battery which may also be rechargeable and which may be similar to the primary battery or may have a different chemistry, size, capacity, or other characteristic compared with the primary battery. Further, the energy storage module 34 can have energy monitoring and charging circuitry which can be configured to recharge either both batteries, or only one battery, simultaneously or alternating at different moments in time, and/or according to a schedule. For example, recharging may only be scheduled (e.g., by an EXD device) to occur when a medical device, powered by the energy storage module 34, is not scheduled to monitor activity or provide therapy (e.g., recharging can occur only during times when a patient is normally asleep). The energy storage module can recharge one battery and simultaneously supply power to the device, or this can be done by a second battery which is not being recharged. A transmitter/communication module 36 can provide for data transmission, reception, and can generally provide for communication with devices which are a part of the wireless power system (network), including one or more power transmitters 12. A power receiver control module 38, which may be programmable, can control all of the other modules of the power receiver module 10A.

In the embodiment of FIG. 2A, a single signal antenna 14C is used both for energy harvesting and for deriving an energy profile. The power receiver control module 38 can electronically disconnect the energy profile module 32 from the antenna 14C so that all the received energy flows to the energy harvesting module 30A. Although connections are only shown between the antenna 14C and modules 30A and 32, the antenna and all the modules of the power receiver module 10A can be functionally connected to, and controlled by, the PRC 38. The particular connections shown in FIG. 2A, are shown to highlight unique features of that embodiment, as is the case for FIGS. 2B-2E. The data communication and transmission module 36 may also be connected to the antenna 14C either directly, or via a connection that travels through the circuitry a different module, such as the energy profile module 32. If the antenna 14C contains any adjustable parameters such as variable programmable resistors which can be used to alter the resonance of the antenna (i.e., the properties of the 'rectenna'), then these can be controlled by the PRC 38.

Figure 1C:
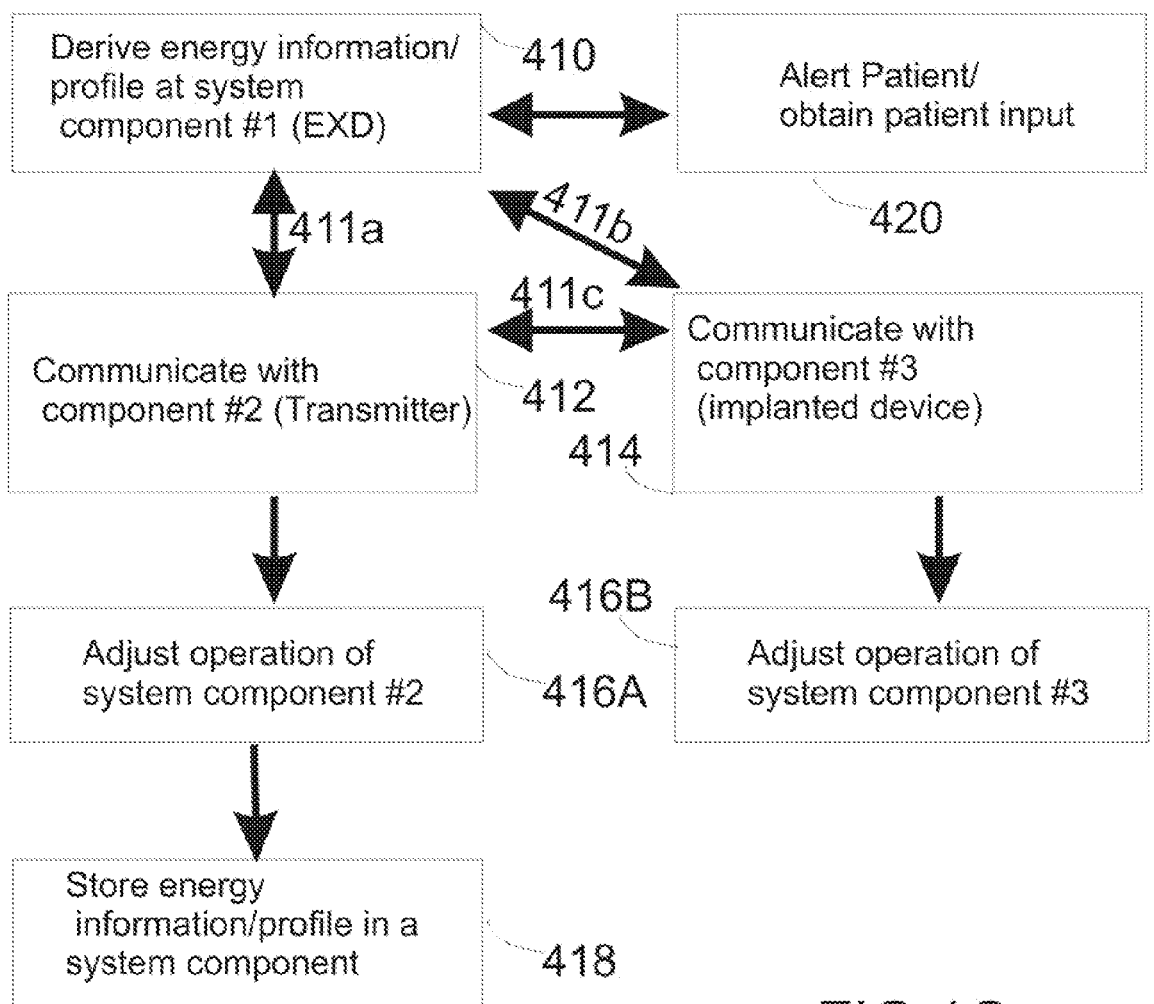

In one embodiment, the energy profile module 32 analyzes energy profiles and determines the (harvesting/transmission) settings which would optimize the wireless energy available. The PRC can then adjust the characteristics of the energy harvester module 30 (such as spectral ranges of energy which are harvested, or temporal patterns across which energy is being received or transmitted by a wireless transmitter 12) in order to improve wireless power harvesting. Since different companies may provide transmitters that transmit energy at different frequencies and using different protocols, the functionality of determining how wireless energy is being transmitted is important for increasing the universal utility of energy harvesting systems. When information about the transmission protocol is communicated by a transmitter either as part of the power signal or as a separate data stream, then the module 32 can decode this information rather than sensing and deriving the characteristics of the energy. Further, the PRC 38 can change the characteristics used for data transmission (when the PRC is in a device that transmits data) based upon such factors as the characteristics of the power transmission profiles. For example, when wireless energy is transmitted at 900 MHz then data may be transmitted at 2.4 GHz. While, in another protocol, if power is transmitted at 60 Hz, then data can be transmitted at 900 MHz. Being able to assess the characteristics of the wireless power which is being transmitted can enable the power receiver device to adjust its energy harvesting operations, or can enable the receiver to send information to the power transmitter 12 in order to adjust the protocol of the data transmission module. In one illustrative embodiment, the energy profile module 32 analyzes energy profiles and determines the settings which would optimize the wireless energy available. The PRC 38 can then use the transmitting module 36 to send data or commands to a power transmitter 12, which can use this information to adjust the energy transmission profile which determines the characteristics of the energy it is transmitting. This may occur with a calibration routine in which several transmission parameters are iteratively adjusted, and evaluated, and then the parameter values which resulted in improved power harvesting can be used (see FIG. 1B-1C). This type of calibration operation can occur periodically, can be automatically or patient initiated by way of the EXD, or can be triggered if power harvesting falls below a selected level, which can occur, for example, when the energy harvester is implanted within a patient who is moving to different locations at different times.

Figure 2B:
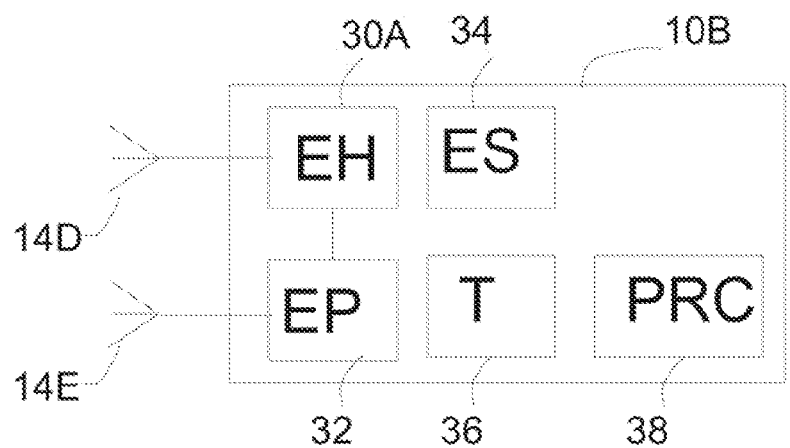

FIG. 2B shows a wireless power receiver module 10B having an antenna 14D functionally communicating with an energy harvesting module 30, and an antenna 14E functionally communicating with an energy profile module 32. The antenna 14E can be used for deriving energy profiles, and can be functionally utilized by the energy harvesting module 30A when this is not necessary. In one embodiment the antenna 14E can be configured especially for sensing over a wide range of spectral energies, as well as, or with priority over, having characteristics related to harvesting power.

Figure 2C:
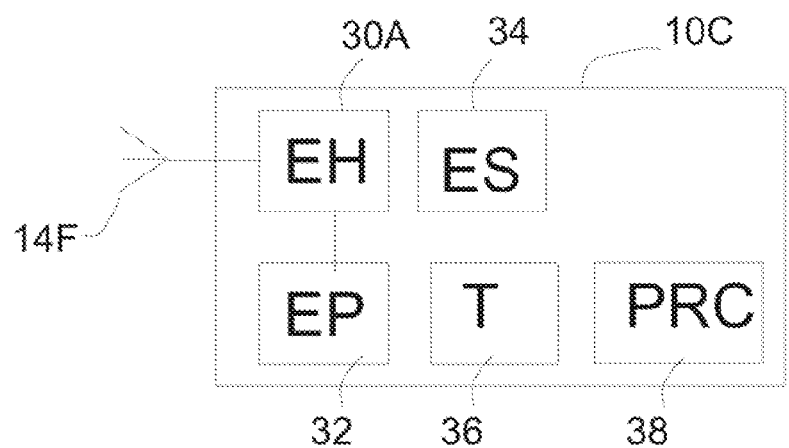

FIG. 2C shows a wireless power receiver module 10C having an antenna 14F functionally communicating with an energy harvesting module 30A, and also serving as an antenna 14F for the energy profile module 32, when this communication is established through the circuitry of the energy harvesting module 30A. Alternatively, or additionally, the energy harvester module 30A can send power to the energy profile module 32, and the energy profile module can measure this power to monitor power conversion which occurs as a function of different types of ambient or transmitted energy signals.

FIG. 2D shows a wireless power receiver module 10D having an antenna 14G functionally communicating with an first energy harvesting module 30A, and an antenna 14H functionally communicating with an second energy harvesting module 30B. The first and the second energy harvesting modules 30A and 30B can be designed to harvest different types of wireless energy efficiently (e.g. energy from different portions of the RF spectrum). For example, energy harvesting module 30A can be used to harvest energy in the 900 MHz frequency range, while energy harvesting module 30B can be used to harvest energy in the 2.4 GHz range. Alternatively energy harvester module 30A can be configured for near-field induction-type wireless energy harvesting, while energy harvester module 30B, can be configured for non-near-field wireless energy harvesting (an may operate with a different protocol). Alternatively, energy harvester module 30A can be configured for strong-signal wireless energy harvesting (e.g. transmitted energy with structured energy signature), while energy harvester module 30B, can be configured for weak-field wireless energy harvesting (e.g., ambient energy of diffuse energy signature). Additionally, energy harvester module 30A can be configured for inductive near-field wireless energy harvesting, while energy harvester module 30B, can be configured for medium-range wireless energy harvesting. Alternatively, energy harvester module 30A can be configured for energy harvesting related to power supply recharging operations, while energy harvester module 30B, can be configured for energy harvesting related to directly powering a device for functional operation. Use of two different energy harvesting modules 30A, 30B can also be configured to differentially charge different types of rechargeable batteries (e.g. some medical devices have two different types of cells for performing different operations) in different manners using circuitry which produces at least partially unique powering characteristics, such as voltage or current ranges. This type of configuring may be especially important when two or more batteries of different capacities, chemistries, and/or characteristics are provided in the energy storage module 34. When multiple batteries do not have matching capacities or characteristics then jointly charging these may lead to unexpected results and reduced efficiencies.

FIG. 2E shows a wireless power receiver module 10E having an antenna 14I which normally communicates with a first energy harvesting module 30A, and an antenna 14J which normally communicates with a second energy harvesting module 30B, both passing through a signal router 42, which can be controlled by the PRC 38 or otherwise. Modules 30A and 30B can each be primarily designed to harvest energy in a particular range, or which is transmitted in a particular manner. However, in the case where the transmitted energy is biased so that energy is primarily being harvested by one or the other energy harvesting module 30A, 30B then the signal router 42 can route both antenna 14I, 14J, to only one of the energy harvesters 30A, 30B. The signal router 42 can also be used to connect the antenna 14I, 14J to energy profile modules, transmission modules, and other modules of the wireless power device 10E (connections not shown in figure to avoid cluttering), or to the device within which the power receiver module 10E is functioning (e.g. to the circuitry of a cell-phone, implanted medical device, radio, or other powered device). Although signal-router 42 is realized here as outside of the PR module 10E, and as attached to antennae 14I, 14J, the router can be implemented within the module, or the housing of the module, as is the case for the antennae.

Open Systems and Methods for Wireless Power

Systems and methods are needed for generic implementation of wireless power systems. Rather than requiring manufacturers or consumers to "buy into" brand specific standards, and circuits (i.e. 'closed system' implementation), various embodiments can allow 'open' systems and methods to be used, leading to more universal utilization of wireless power devices.

Figure 3A:
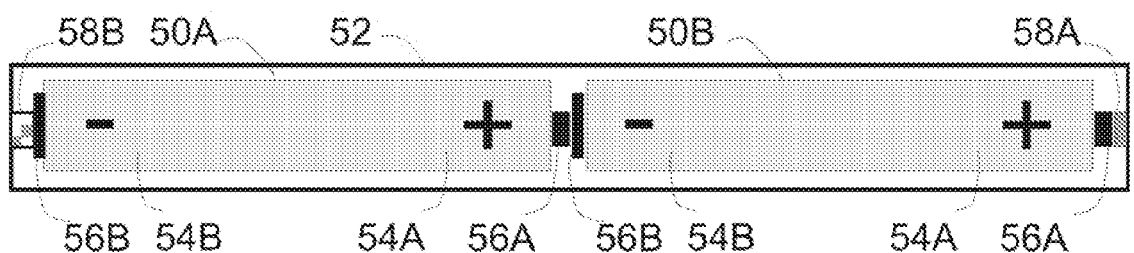
FIG. 3A illustrates a schematic diagram of two AA batteries contained within an AA series-type storage housing.

FIG. 3A illustrates a schematic diagram of two AA batteries 50A, 50B which reside within a conventional storage housing 52 for AA "serial-type" storage. Each battery 50 has a positive ('+') and negative ('−') region 54A and 54B, ending in a positive terminal 56A and negative terminal 56B, respectively. The positive terminal 56A communicates to a positive terminal contact 58A of the compartment, and the negative terminal 56B communicates to a negative terminal contact 58B. As is well known these contacts may be a conductive spring, flexible leaf member, or may be simply rigid. When more than one battery 50 occurs in series, then the positive terminal 56A of one battery 50A may contact the negative terminal 56B of another battery 50B rather than communicating to a positive terminal contact 58A. An example of a device that may implement this type of configuration is a small flashlight.

Figure 3B:
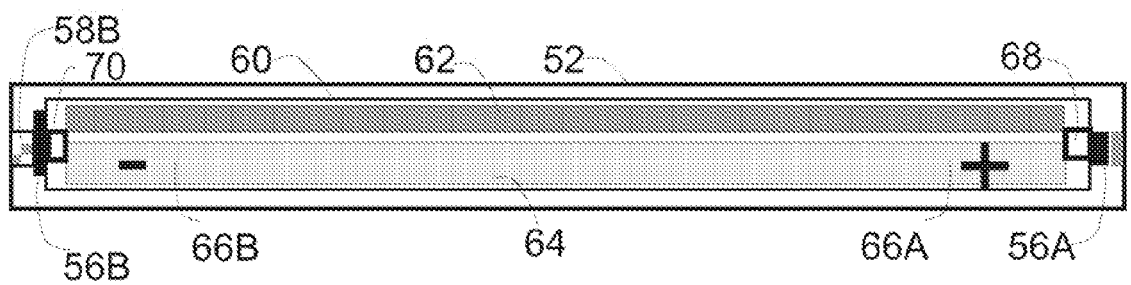
FIG. 3B illustrates a schematic diagram of the present invention wireless power-pack having a harvesting module and a rechargeable primary battery which can be recharged from the harvesting module.

The batteries 50 can be alkaline batteries such as the MN1500-LRS made by Duracell which produces 1.5 volts, or can be rechargeable using Lithium Ion (e.g., polymer) or Nickel metal-hydride NIMH, such as the DR-10 made by Duracell. The batteries 50 can also be D, C, AAA, N, 9V, or other type of battery housed in a respectively appropriate storage housing 52. The storage housing 52 can be configured to hold 1, 2, 3, 4, 6, 8, or any other number of these batteries, as well as batteries that are cylindrical, button, stack, coin, lantern prismatic, bulk packaged, or of other geometry. Accordingly, the shape of the wireless rechargeable-power supply device 60 of FIG. 3B is realized so as to reside within one of these storage housing 52 geometries without requiring a modification of the device or the housing 52. The power-supply device 60 may be less than the length of the embodiment illustrated, for example, preferably half as long.

FIG. 3B illustrates a schematic diagram of the present invention wireless rechargeable-power supply device 60 having a harvesting module 62 and a rechargeable primary battery 64 which can be recharged from the harvesting module 62. The rechargeable primary battery 64 has a positive ('+') and negative ('−') regions 66A, 66B, ending in positive terminals 56A and negative terminals 56B, respectively. A positive side junction 68 can electrically connect the power harvester 62 directly to the positive terminal 56A (for directly powering a device), or can connect the positive side 66A of the primary battery 64 directly to the positive terminal 56A (for powering the device from the battery), or both. The positive side junction 68 can also serve to electrically connect the power harvester 62 to the primary battery 64 in order to provide recharging functionality, which may further entail disrupting power transmission to the device during recharging operations. The positive-side junction 68 can be a simple electrical connection, such as a metallic connection, or may be a simple routing circuit (including 1 or more diodes), or may be an active/programmable/controllable circuit which is controlled by external control signals sent from the device which is being powered 5 (not shown) or by a power transmitter 12. Generally, these connections may be supplied in a fixed, dynamic, and/or programmable manner, and may be provided in a user/device controlled manner if the required circuitry is provided (e.g. similar to 88, 89 of FIG. 6B). The connection junctions 68, 70 may also be configured to enable charge to be routed to the rechargeable battery 64, when battery recharging is provided by the device 5 using conventional non-wireless methods (i.e. using conventional 'plug-in' charging for the device). The junctions 68, 70 may also be configured to provide: electrical isolation to occur, for example, during recharging of the battery; low pass filtering of output voltage signals; and, voltage regulation. The wireless rechargeable-power supply device 60 may be designed to use allocate various proportions of its volume to the power cell and the wireless harvesting components depending upon performance-related considerations. As in other figures of this applications, the components of FIGS. 3A-3E are not limited to the illustrated to scale or geometry shown, and, as taught, can also be realized partially external to the power supply device 60.

Similar to the positive side junction 68, a negative side junction 70 can electrically connect the power harvester 62 directly to the negative terminal 56B (for directly powering a device via wireless power), or can connect the negative side 66B of the primary battery 64 directly to the negative terminal 56B (for powering the device from the battery), or both. The wireless rechargeable power supply device 60, may also be realized without the negative and positive side junctions 68, 70, and the rechargeable battery may simply be connected to the positive 56A and negative 56B terminals (and functional connection with the power harvester module may be realized using alternative connections formed elsewhere within the supply device).

In the illustrated embodiment the wireless rechargeable-power supply device 60 has approximately the length of two serially positioned AA batteries 50A, 50B and fits into the battery compartment 52. This enables the wirelessly rechargeable battery 60 to supply power to a user device 5 which normally accepts two AA batteries in a series type configuration. In a preferred embodiment the power supply device 60 has the approximate shape of an AAA battery being 44.5 mm long and 10.5 mm in diameter. In an alternative preferred embodiment the wirelessly rechargeable battery 60 has the approximate shape of an AA battery being 50.5 mm long and 13.5-14.5 mm in diameter. In an alternative preferred embodiment the wirelessly rechargeable battery e 60 has the approximate shape of a C type battery being 50 mm long and 26.2 mm in diameter. In an alternative preferred embodiment the wirelessly rechargeable battery 60 has the approximate shape of a D type battery, being 61.5 mm long and 34.2 mm in diameter. In another alternative preferred embodiment the wirelessly rechargeable battery 60 has the approximate shape of a multiple (N) of common battery types. For example, setting N=2, results in a 89 mm length (i.e. 2×44.5) and 10.5 mm diameter as shown in FIG. 3B, which fits within existing battery storage compartments designed to hold 2 AA type batteries in a serial manner. This can also be done to accommodate parallel-type configurations of battery storage compartments. This can also be done to accommodate battery storage compartments which are a mixture between serial-type and parallel-type. These embodiments enable wireless power devices 60 to be created which utilize existing power compartments without requiring specialized modifications of the devices which they are powering. This is a great advantage over requiring manufacturers to modify and adapt their designs in order to incorporate wireless power recharging features into their products.

Figure 4A:
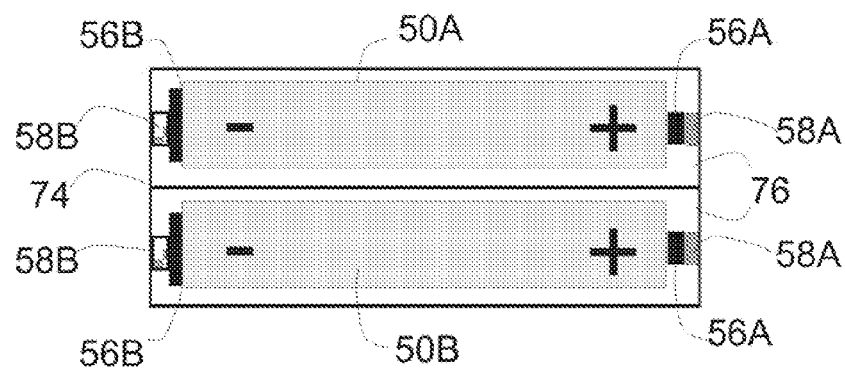
FIG. 4A illustrates a schematic diagram of two AA batteries residing within an AA parallel-type storage housing.

FIG. 4A illustrates a schematic diagram of two AA batteries 50A, 50B residing within an AA parallel-type storage housing 72, which contains a shallow ridge 74 which serves to separate the batteries 50A, 50B, and which may also assist in defining 2 slightly beveled regions 76 having cylindrical shaping. The batteries have a positive ('+') and negative ('−') regions, ending in positive terminals 56A, and negative terminals 56B, respectively. The positive terminal communicates to a positive terminal contact 58A and the negative terminal 56B communicates to a negative terminal contact 58B, each of which may be a spring, conductive and flexible leaf member or simply conductive. When more than one battery 50 occurs in series, then the positive terminal of one battery 50A may contact the negative terminal of another battery 50B rather than communicating to a positive terminal contact 58A.

Although this example utilizes AA battery type, the batteries 50 can be, and can be shaped like, alkaline batteries such as the MN1500 LRS made by Duracell which produces 1.5 volts, or can be rechargeable using Lithium Ion (polymer) or Nickel metal-hydride NIMH, such as the DR10 made by Duracell. The batteries 50 can also be D, C, AAA, N, 9V, or other type of battery housed in a respectively appropriate storage housing 52. The storage housing 52 can be configured to hold 1, 2, 3, 4, 6, 8, or any other number of batteries, as well as batteries that are cylindrical, button, stack, coin, lantern prismatic, bulk packaged, or of other geometry. The wireless rechargeable-power supply device 60 can be implemented in accordance with any of these forms and may utilize or work with mixtures of rechargeable cells and non-rechargeable cells, and can be implemented in battery compartments 52.

Figure 4B:
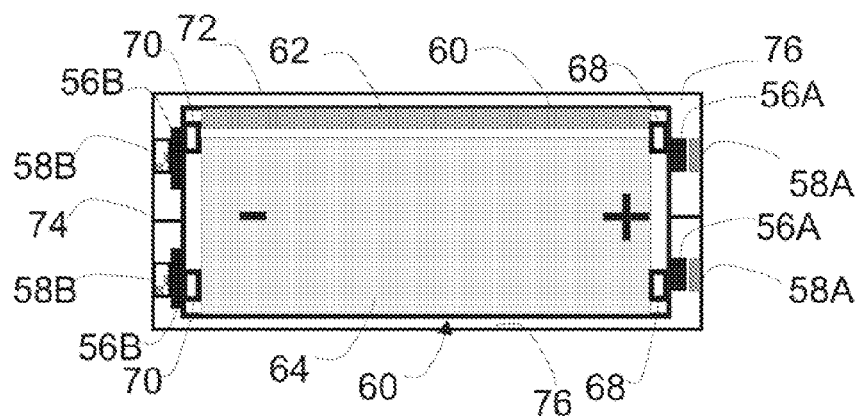
FIG. 4B illustrates a schematic diagram of the present invention wireless power-pack configured to reside within an AA parallel-type storage housing.

FIG. 4B illustrates a schematic diagram of the present invention wireless-power harvesting device 60 which is configured to reside within an AA parallel-type storage housing, and has physical dimensions in accordance with this aim. In this preferred embodiment, the wireless-power harvesting device 60 is realized as a single device that spans the area normally reserved for 2 separate batteries. The rechargeable battery 64 assumes the majority of the internal volume of the device 60 relative to the energy harvesting module 62, but the opposite may be true, or both 62, 64 may utilize approximately equal volumes. Additionally, the energy harvesting module 62 and rechargeable battery 64 do not have to be positioned in a parallel fashion, but can be configured using any geometry within the internal portions of the wireless-power harvesting device 60. Although the positive and negative contacts 56A, 56B are located on the right and left sides of the device 60, rather than being located oppositely, the device can comprise a single side configured with both negative and positive contacts 56A, 56B (as can occur with anti-parallel or 9-volt configurations). This feature can be provided using one of several possible design adjustments. For example, two or more conductive elements may be provided which traverse the length of the device 60 and communicate a particular charge polarity to the contacts 56 of the device. Alternatively, the internal design of the device 60 may be altered (to provide both negative and positive polarities on the same side of the device, rather than on opposite sides) as is shown in FIG. 5C. In that embodiment, the two wireless power energy harvesting modules 62 are each configured oppositely with respect to the rechargeable batteries 64A, 64B as a function of the relative positions of the positive and negative terminals. Additionally, when a single power harvester module 62 is used to harvest energy for 2 different rechargeable batteries, having opposite polarities on the same side of the device, a voltage inverter can be used to provide the correctly polarized charge to the respective half-cells of the rechargeable battery. The device shown in FIG. 4B may be realized with an anode and cathode on the left and right sides of the rechargeable battery 64, and may have both anode and cathode terminals on the same side, and this may be realized by a single cell, or by several cells as are shown in FIGS. 5B-5D.

Figure 4C:
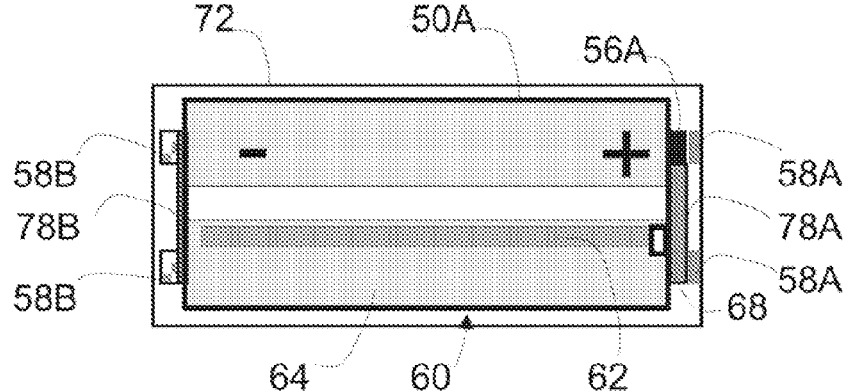
FIG. 4C illustrates a schematic diagram of an alternative embodiment of the present invention wireless power-pack configured to reside within an AA parallel-type storage housing.

FIG. 4C illustrates a schematic diagram of an alternative embodiment of the present invention wireless rechargeable-power supply device 60 configured to reside within an AA parallel-type storage housing and to also power a conventional rechargeable battery. The device 60 is configured with a rechargeable battery 64 and an energy harvesting module 62. There is at least one of a positive conductor flap 78A and a negative conductor flap 78B on the positive and negative terminal end of the wireless rechargeable-power supply device 60. These flaps make contact, respectively, with terminal contacts 56A and 56B, of the battery storage casing 72 to power the device 5. The positive conductor flap 78A also makes contact with the positive terminal 56A of the conventional rechargeable battery 50. Similarly, the negative conductor flap 78B also makes contact with the negative terminal 56B of the conventional rechargeable battery 50. In this manner the wireless rechargeable-power supply device 60 can both supply power to the device 5 and also serve to re-charge the conventional rechargeable battery. In an alternative embodiment, the wireless rechargeable-power supply device 60 only contains an energy harvesting module 62, and the device 5 may be configured to differentially draw power from a conventional rechargeable battery 50 or the wireless component depending upon the relative energy available. In this realization a rechargeable-power supply device 60 comprises a power harvesting component which resides within the battery storage housing; a first conductor flap configured to extend to the negative terminal of a rechargeable battery; and a second conductor flap configured to extend to the positive terminal of a rechargeable battery. The first conductor flap may also be configured to make contact with at least one battery terminal of the device's battery compartment configured for receiving the negative terminal of a battery. The second conductor flap may also be configured to make contact with at least one battery terminal of the device's battery compartment configured for receiving the positive terminal of a battery. The rechargeable battery supply can be configured to reside within the battery compartment without requiring any alteration of the back-plate of the device 5 which it powers.

Figure 5A:
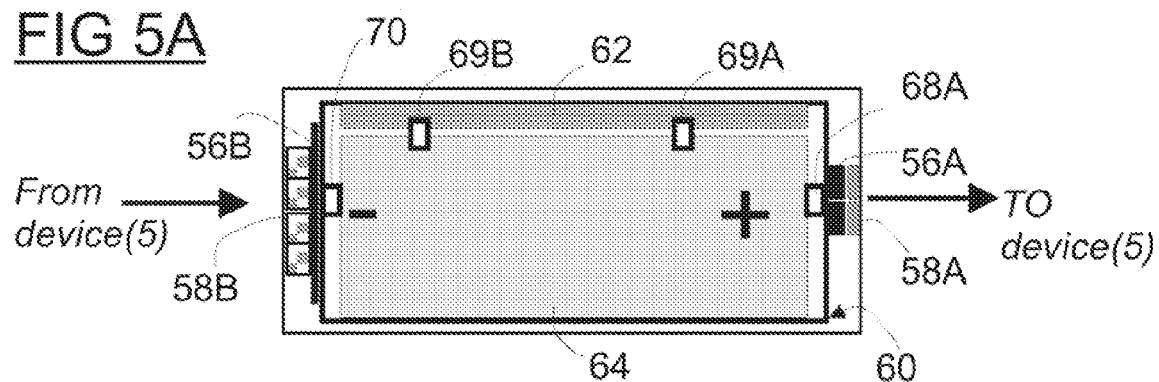
FIG. 5A illustrates a schematic diagram of the present invention wireless power-pack comprising a harvesting module and a rechargeable primary battery, and configured for charging the primary battery, providing power directly to a device, and jointly powering a device.

FIG. 5A illustrates a schematic diagram of the present invention wireless rechargeable-power supply device 60 comprising a harvesting module 62 which is configured for charging the primary rechargeable battery 64, providing power directly to a device 5, and/or jointly recharging and powering a device 5. In the illustrated embodiment, the wireless rechargeable-power supply device 60 contains positive side charging circuitry 69A for charging a positive portion of the battery, and negative side charging circuitry 69B for charging a negative portion 66B. The circuitry 69 may simply be electrodes that make electrical contact with the positive or negative cell of the rechargeable battery and the corresponding positive/negative contacts (e.g. labeled "+" and "−" of FIGS. 12A-D, or respectively charged sides of a capacitor) within the harvesting circuitry. Charging can occur using a first harvesting module and a second harvesting module each designed to provide a different voltage or polarity. The first harvesting module may be configured for far field wireless power reception and the second harvesting module may be configured for near-field, inductive-type harvesting.

Figure 5B:
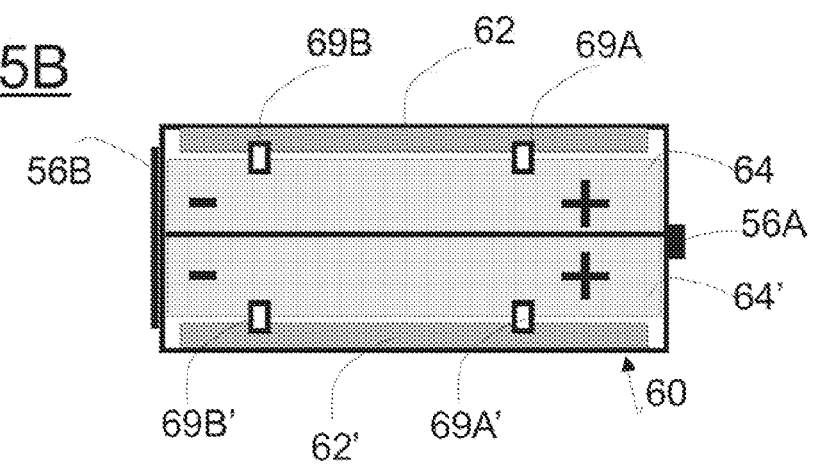
FIG. 5B illustrates a schematic diagram of an alternative embodiment of the present invention wireless power-pack comprising a $1^{st}$ harvesting module harvesting module configured for charging the primary battery, a $2^{nd}$ harvesting module configured for charging the secondary battery, providing power directly to a device, and jointly powering a device.
Figure 5C:
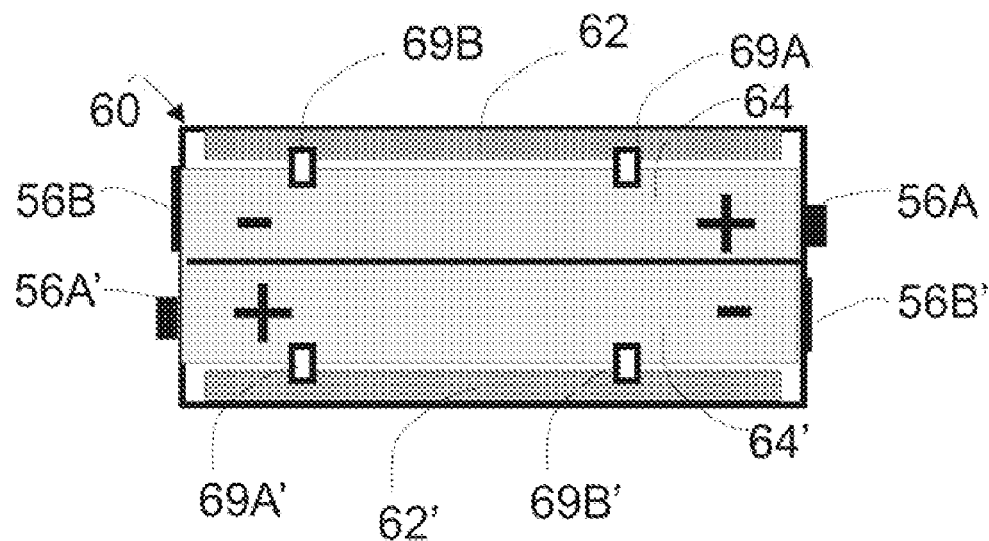
FIG. 5C illustrates a schematic diagram of an alternative embodiment of the present invention wireless power-pack comprising wherein the primary and second battery are oriented in opposite directions.
Figure 5D:
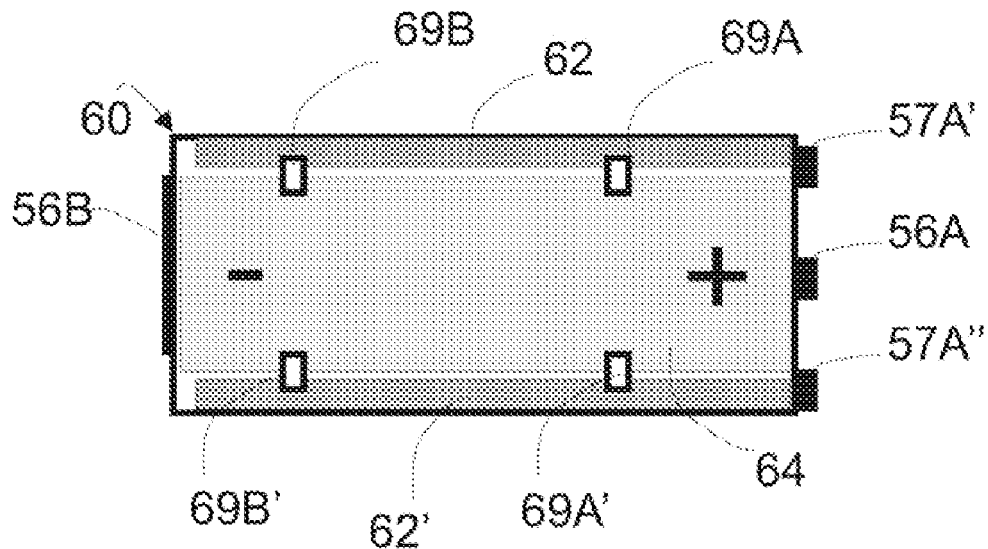
FIG. 5D illustrates a schematic diagram of an alternative embodiment of the present invention wireless harvesting device comprising a $1^{st}$ harvesting module, a $2^{nd}$ harvesting module, and a rechargeable primary battery each of which provide an output terminal.

FIG. 5B illustrates a schematic diagram of the present invention wireless rechargeable-power supply device 60 comprising a first harvesting module 62 for recharging a primary rechargeable battery 64, and a second harvesting module 62' for recharging a secondary rechargeable battery 64. In the illustrate embodiment, the two batteries may have similar or different characteristics. The harvesting modules 62, 62' can be configured in line with these characteristics. Alternatively, multiple harvesting modules 62, 62' can be used to charge a single rechargeable battery 64. When two harvester modules are used then the primary antenna orientation for the first harvester may be aligned between 45 or 135 degrees relative to the secondary antenna orientation so that one of the batteries will always be relatively more aligned with the orientation of the transmitted wireless energy.

In FIG. 5C the power supply device 60 has harvesting modules 62, 62' which are configured to provide power to a first and second rechargeable battery 64, 64' which have opposite orientations for their positive 56A, 56A' and negative 56B, 56B' terminals. In other words, the power supply device 60 can be configured so that multiple terminals of different polarities occur on the same side of the device in order to provide equivalent charging schemes to what occurs when using separate conventional batteries. Harvester connections 69A and 69B, as well as the harvester 62 circuitry should be arranged to provide the respective charges to the positive and negative portions of the battery.

In FIG. 5D the power supply device 60 has at least a first or second harvesting module 62, 62' each of which is configured to provide power to a first rechargeable battery 64 which provides power as normally accomplished using 3 batteries configured in parallel, and therefore has three positive terminals (56A, 57', 57") and one extended-negative 56B terminal which make functional contact with a conventional-type of battery compartment shaped to house three batteries.

Figure 6A:
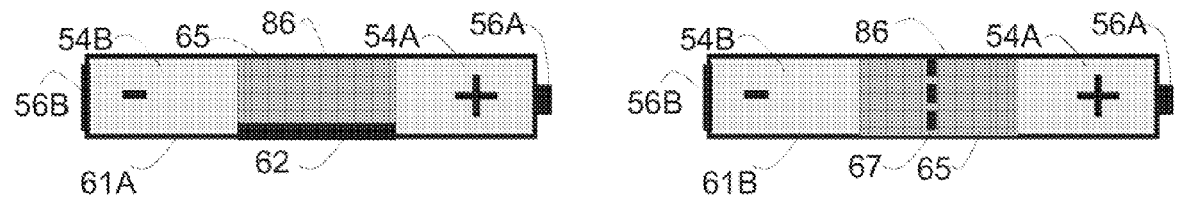
FIG. 6A illustrates a schematic diagram of a rechargeable battery having a surface configured for wireless power reception.

FIG. 6A illustrates, on its left side, a schematic diagram of a rechargeable battery 61A configured with a centrally located 'accessory plate' 86, which can be physically and electrically isolated from the positive and negative contacts 56A, 56B and can also be electrically isolated from the battery housing. The centrally located 'accessory plate' 86 can serve as an antenna which harnesses wireless power for harvesting circuitry 62 that exists within battery 61A. Alternatively, on the right side of the figure, a rechargeable battery 61B is shown with a centrally located 'accessory plate' 86, that can serve as a power transfer surface which operatively achieves power transfer from power already harvested using an externally disposed wireless harvester module 90 (not shown). The accessory plate 86 can have at least two electrically isolated components created via non-conductive barriers 67, and each component of the accessory plate can conduct energy to a part of the battery such as the anode and cathode components, or a control circuit.

A wireless harvester module 90 can be provided which can be designed to harvest wireless energy using at least one of near or far field methods and then transmit the power to the 'accessory plate' 86 of the rechargeable battery 61b. The external wireless harvester module 90 can be located within or external to the housing of the device 5, and can provide a power-line 92 (not shown), which may contain a positive, negative, and/or ground line, to the 'accessory plate' 86. In this embodiment the 'accessory plate' 86 may be electrically realized in segments each of which can receive a different type of power or polarity (i.e., negative/positive/ground), and may also have surfaces which can receive control signals. The 'accessory plate' 86, in turn relays power to the rechargeable battery 61b, such as to the positive and negative regions of a cell. This embodiment therefore utilizes at least one centrally located 'accessory plate' 86 which may be realized as a centrally disposed conductive terminal which is not used for charging the device 5, but rather for recharging the wirelessly rechargeable battery.

If the centrally located 'accessory plate' 86 is an antenna, or is connected to an antenna, then an energy harvester module 62 would be located inside of the rechargeable battery 61a. Alternatively, if the centrally located 'accessory plate' 86 receives at least one type of charge from an externally located power harvester module, the rechargeable battery 61b is more simply designed to merely receive the one, two, or more charge polarities and to then charge the cell(s) of the rechargeable battery 61b. The accessory plate 86 may be electrically compartmentalized by electrical barriers 67 into a plurality of distinct regions configured to receive different types of charge (e.g. different polarities, voltage levels). Various mechanical components can be used to secure external components to the accessory plate 86 (and to ensure proper connection to the respective regions which are defined within the plate). These may include spring biased mechanisms, lock and key physical constraints, and the like.

Figure 6B:
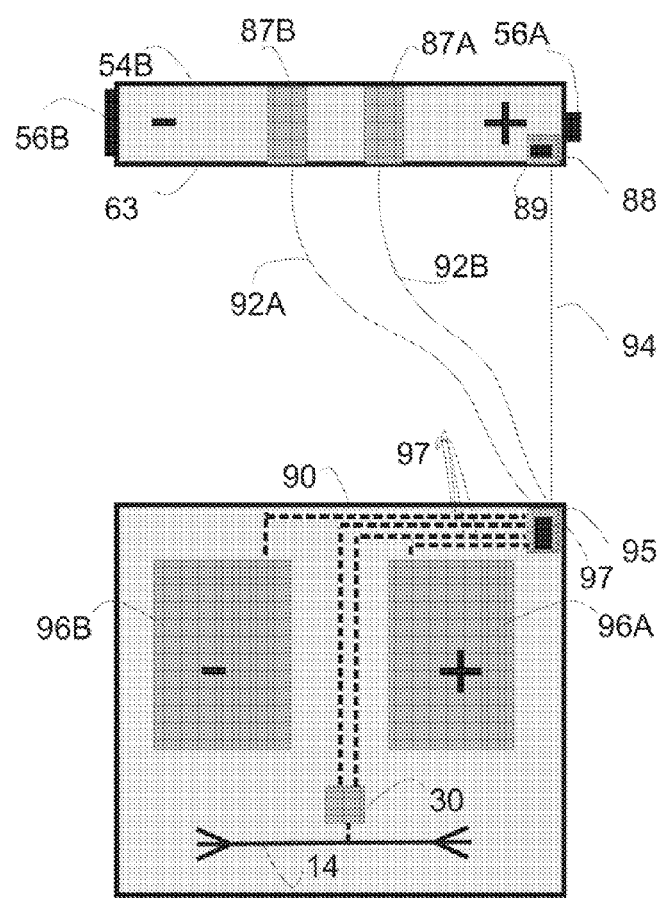
FIG. 6B illustrates a schematic diagram of a rechargeable battery having a plurality of surfaces configured to work in conjunction with the illustrated wireless harvester module accessory.

FIG. 6B illustrates a schematic diagram of a rechargeable battery 63 having at least two physically distinct power transfer surfaces 87A, 87B, which are configured to accept positive and negative power-lines 92A, 92B, and to work in conjunction with the illustrated wireless harvester accessory module 90. In this embodiment, the wireless harvester accessory module 90 comprises positive and negative induction components 96A, 96B, which are configured to operate with induction pads provided by companies such as Splashpower. The harvester accessory module can be tucked into the battery storage component if there is sufficient room or can exist outside the device, such as being a part of a customized cell-phone back-plate in the case of a cell-phone. In this manner, any device can use generically-configured induction pads to re-charge the rechargeable batteries without requiring modification of the device 5 within which the batteries reside. The external wireless harvester accessory module 90 may also have a communication/control module 95 which is designed to control charging operations in a fixed or programmable manner communication/control module 95 may be controlled by: a) control signals that are sent from a wireless transmitter and received from an antenna; b) control signals which are sent via modulation of the wireless power signals (wherein the modulation serves as the control signals when these are decoded via module 95); and c) control signals that eminate from the rechargeable batter itself and which are transmitted over control line 94. The communication/control module 95 can send a control line 94 to a control surface 88 of a customized rechargeable battery in order control recharging circuitry 89 which is designed to modify and monitor features and functions of the wireless rechargeable battery 63, in recharging/power operations. The control surface 88 can be implemented as a port/plug if there is sufficient room for this to occur: in this case the control line 94 is provided with a complementary plug for allowing connection thereto. The control recharging circuitry 89 may include circuitry for monitoring or adjusting:

a) the functional the drain on the battery;
b) the internal resistance of the cells;
c) the rate of charge over time;
d) the amount of charge used for recharging the battery cells or which is directly diverted to the device which is being powered;
e) the overload circuitry for breaking circuits when the recharging power has unwanted features (e.g., incorrect polarity or voltage level);
f) the temperature monitoring and temperature-cut-off means which prevents recharging operations (or battery use), from occurring when temperatures exceed a specified range;
g) the impedance-matching means;
h) isolation components which can isolate the cells from the battery terminals when recharging occurs (for example, in order to keep charge from leaking to adjacent batteries which may not be rechargeable);
i) the components for performing "battery full operations" such as attenuating or halting recharging operations; and,
j) the components for sending control signals to the wireless harvesting module.

Recharging, both here and as provided by other components of the invention may occur using a 'fast charge' protocol to charge a power supply to 80% capacity, and then switch to 'trickle charging' for toping off. Some of these features of the control re-charging circuitry 89 may be realized jointly with, or primarily/wholly by, the communication/control module 95 of the power harvesting accessory 90 and even the wireless power transmitter.

The communication/control module 95 accepts electrical connections 97 from the induction-type 96 and antenna-type 14,30 power receivers and communicates the power signals to the power transfer surfaces 87A, 87B by way of positive and negative power-lines 92A, 92B which are fastened to, or biased against, the transfer surfaces by various means. The communication/control module 95 may also have signal conditioning element such as low-pass or high-pass filters (as may be implemented by way of capacitors) that serve to block certain energy frequencies from being transmitted from the harvester accessory 90 to the device 5 and/or its wireless rechargeable batteries 63. Power-lines 92A, 92B, can also be configured to terminate in a number of plugs which are configured to work with different devices 5 and wireless batteries 63.

Accordingly, in the preferred embodiment shown there is provided at least two approximately dedicated 're-charging terminals' (e.g. power transfer surfaces 87A, 87B), that can be located within the housing of each rechargeable battery 63. These surfaces may be universally positioned, or can be realized using 2 or 3 generally accepted variations. For example, when transfer terminals 87A, 87B are spaced 2 mm apart they configured for accepting power provided within a first range e.g. (1-2 volts), while intra-terminal spacing of 3 mm is provided for a second range (4-6 volt). In one embodiment, the first transfer terminal pair is configured for accepting power harvested from induction-type charging, which is generally larger than power harvested from transmitted power. The power-harvesting accessory 90 may send different connectors to these two pairs of terminals. In this manner, power accessories 90 can have multiple circuits which are designed to drive different loads and the wirelessly rechargeable batteries will not be incorrectly connected to power-lines 92A, 92B (or their corresponding connector fittings) which have charges above or below what is "expected" by the rechargeable battery. This "charge-specific" feature may also be applied to transfer terminals 87A, 87B if these are realized as plugs with unique geometries. In this case, the transfer terminals 87A, 87B fit-with charge transfer plugs having corresponding geometries which work together as a lock and key system that ensures the intended charging occurs. A main feature of these re-charging terminals is that they allow the wireless harvesting accessory to be attached to the battery without concern for how the battery, in turn, is connected to the device. This solution also does not require the manufacturer to provide sufficient space within devices between the battery and the device contacts, for example, in order to provide room for a charging structure to be implemented therein. The power harvester accessory 90 and its related components can be realized as a replaceable back-cover, which is able to 'snap' onto the device's battery compartment. By using a secondary set of battery contacts which are provided solely for recharging purposes and for interacting with the battery itself, the battery-device interface may remain unchanged. The wireless harvester accessory module may also be configured with a junction plug which can be plugged into a data/power port of a device, such as a cellphone.

Figure 6C:
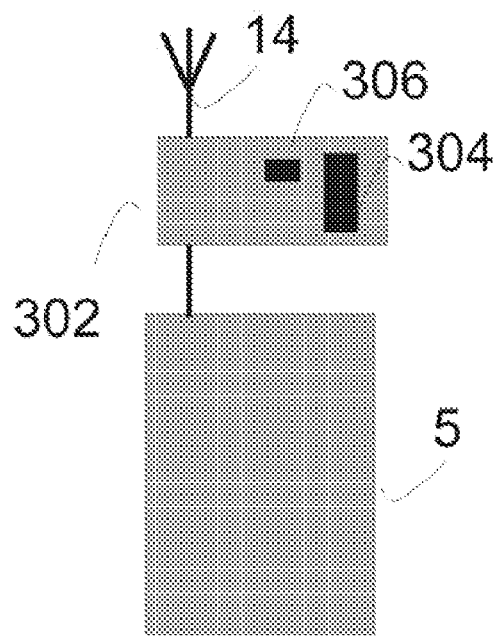
FIG. 6C illustrates a schematic diagram of a 'near-to-far' wireless harvester module, which can also be considered an induction to RF energy converter.

Other types of wireless harvester accessory modules 90 may also be provided. For example, the module can be configured with a converter to convert both near-field and far-field power so as to power devices when the wireless power which is harvested is of either type. For example, if a device is configured to be used with PowerCast technology it may use an antenna which is not able to be charged by the Splash-pad power induction device. By providing a 'near-to-far converter' 302, which is designed to convert the induction-type power provided by near-field induction means (e.g., a positive charged surface and negatively charged surface) into energy which can be harvested by the PowerCast antenna, a device 5 which may be a cellphone, configured for PowerCast type of recharging can be recharged using the SplashPad (this is different from the device of FIG. 6B which includes two types of harvesting elements that harvest power directly rather than converting the wireless power that is harvested using a converter). As shown in FIG. 6C, the 'near-to-far converter' 302 can include an induction-type power harvester 304 which powers an RF power transmission circuit 306 which, for example, transmits at 90 MHz, when powered by the inductive type power sources.

The wireless power accessory can provide power to devices even if these devices are not configured with power transfer surfaces 87A, 87B to accept the power-lines 92A, 92B. For example, the 'near-to-far converter' 302 can be configured as a small box that 'clips onto' the antenna of a PowerCast wireless power receiver (which may be a headphone cable of an mp3 player, or a power-accessory antenna of a different device). It is also possible to provide a 'far-to-near converter' 308, which receives far-field power which is transmitted by a wireless power transmitter and then converts this to power which is then supplied by an induction surface either directly, or by way of an intermediate storage battery which stores the wireless energy (although this second type of conversion is less robust). In other words a SplashPad-type of device (including its rechargeable battery) may be powered by a PowerCast transmitter. The 'near-to-far converter' 302 can be implemented as an RF transmitter which is powered by a Splashpad device and performs power transmission according to a defined protocol.

Figure 6D:
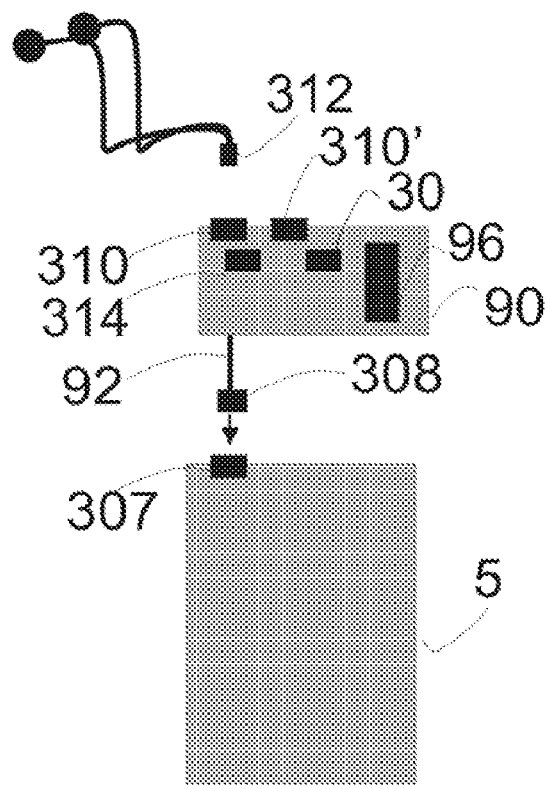
FIG. 6D illustrates a schematic diagram of a power harvesting accessory with an accessory port which is attached to an audio-device which here is an MP3 player.

FIG. 6D shows a wireless power accessory 90 which has power-lines 92 which can terminate using a plug adapter 308 that plugs into a device 5. For example, the plug adapter 308 can be configured as a stereo plug that plugs into an outlet 307 of a sound device such as an MP3 player. The device 5 is configured to be recharged by making a functional connection between the port 307 and a USB port of a computer. This type of plug adapter 308 (or the power accessory 90 itself) may also provide an accessory port 310 which allows the acceptance of the plug of any accessory (in this case a headphone plug 312) which normally plugs into the port 307 of the device 5 (when the port 307 does not receive a plug from a USB power source). This allows individuals to utilize generic-type headphones which has not incorporated a wireless power accessory feature into its design, and to thereby realize this feature for the device 5. Since the 'accessory port' 310 of the accessory 90 allows connection between plug 312 and port 307, the wireless power accessory 90 becomes invisible to the device 5 except that wireless-power recharging that is supplied along with other functionality. The accessory port 310 or wireless power accessory 90 may also be configured with a power control module 314 so that wireless power-recharging doesn't occur when the device is turned on (e.g. when an audio signal is being transmitted to the headphones) in order to prevent malfunction of the device 5. The power control module 314 can also include a button 96 which lets the user control power harvesting and supply operations. The plug adapter 308 can also be implemented to work with power/data ports which normally accept conventional AC/DC chargers for various devices such as an iPhone.

As shown in FIGS. 6B-D, instead of being configured solely for obtaining near-field induction-type from a splash-pad-type wireless charger, the wireless harvester accessory module 90 can harvest either type of power. Wireless power accessory 90 can also be provided with an antenna 14 (or is configured to be used in conjunction with an accessory antenna which may be attached to the accessory module 90 using one or more accessory ports 310,310'), as well as with a power harvesting module 30. Although many embodiments are possible, in a preferred embodiment the external wireless harvester accessory module 90 is incorporated into the lid or 'backplate' which normally covers the battery compartment of a device 5 such as a cell-phone. In another preferred embodiment the external wireless harvester accessory module 90 is incorporated into a protective case which normally surrounds a device 5 such as a cell-phone.

The wireless harvester accessory module 90 may send a control-line 94 to the rechargeable battery 63 (or to the device 5, or both) in order to control and/or monitor recharging operations. In this manner, conventional rechargeable batteries can be used without much modification of the device 5 which is being powered. The external wireless harvester accessory module 90 can also be configured to provide a number of recharging capacities and features to improve recharging operations. Fore example, the wireless harvester accessory module 90 (and other components of the invention e.g., 38 of FIG. 1) can implement 'pulse technology' during recharging in which a plurality of pulses are fed to the battery and wherein each pulse has a strictly controlled rise time, shape, pulse width, frequency and amplitude.

Figure 7A:
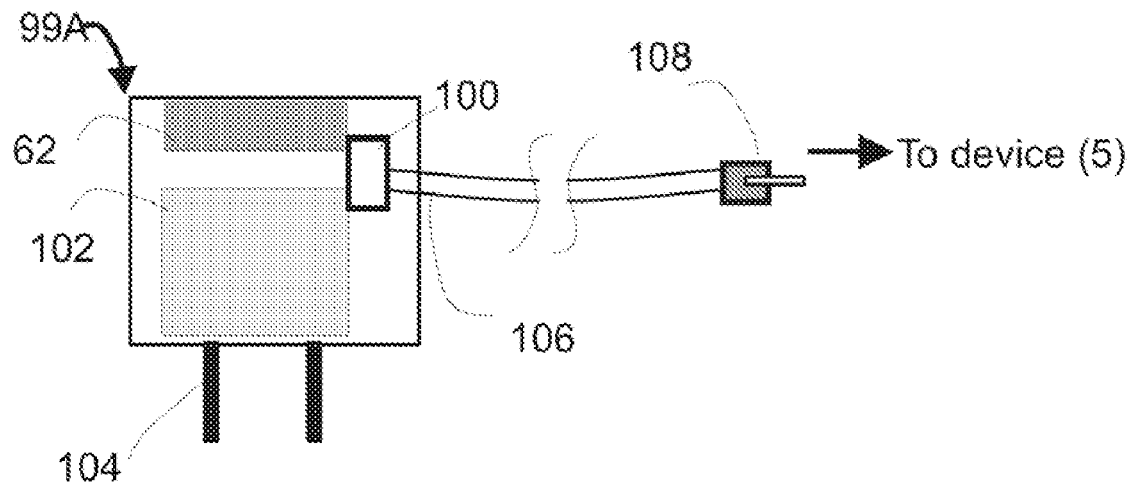
FIG. 7A illustrates a schematic diagram of a power harvesting module implemented within a traditional "wall plug" type of charger.

FIG. 7A illustrates a schematic diagram of a power harvesting module 62 implemented within a traditional "wall plug" type of charger 99A. A power management module 100 accepts recharging power from either the harvester module 62, or an AC/DC converter 102 that converts electricity derived from the plugs 104 which reside within an AC mainsline wall outlet. A power management module 100 outputs DC power through a power cord 106 to charging the device 5 which has a power-port which is configured to accept plug 108. The charger 99A can supply charges, or trickle charges, to a device when wireless power is available and no AC outlet is available (or conveniently available) and can provide normal charging via AC power when this is available. The housing of the charger 99A can further include other features that serve to augment wireless power harvesting such as embedded antenna elements, a deployable-extendible antenna; and indicators such as LED which are combined with monitoring circuitry to enable users to see how much wireless energy is available. The indicator can glow more brightly as the amount of power harvested increases. The charger 99A/99B can include at least one harvester module 62 that is designed to be powered from either near-field induction type or far-field power transmitters, or both. The charger 99A/99B can also contain a wireless-power accessory port (not shown) for accepting input from a power harvesting accessory 90 device.

Figure 7B:
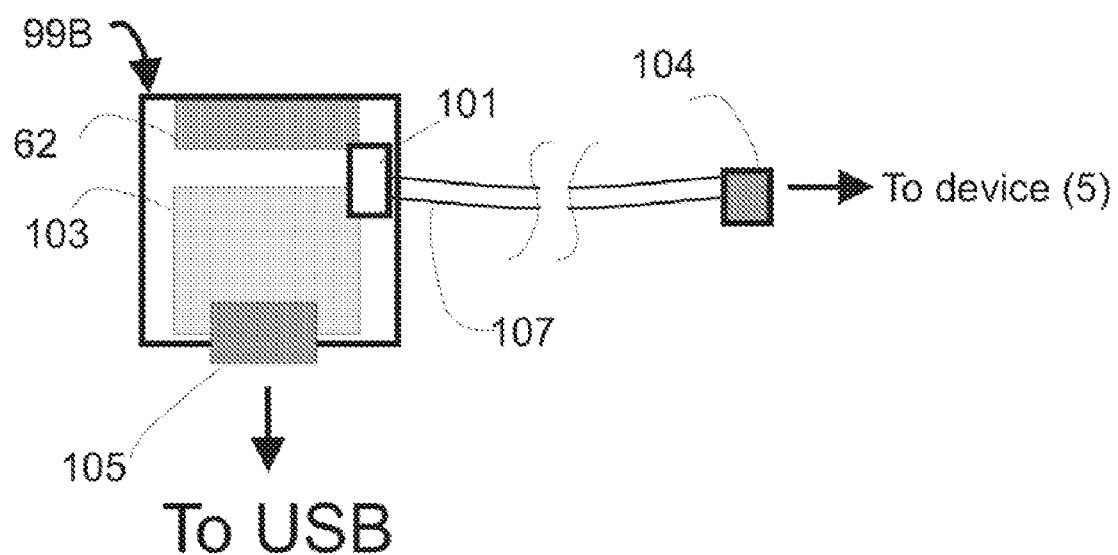
FIG. 7B illustrates a schematic diagram of a power harvesting module implemented within a traditional USB interface charger.

FIG. 7B illustrates a schematic diagram of a power harvesting module 62 implemented within a traditional "USB" type of charger 99B having a USB plug interface 105 which can accept USB power from a portable device such as a computer. A power management module 101 accepts input recharging power from either the harvester module 62, or USB interface connector 103 that that obtains power from USB plug 105. Module 101 then sends power through power cord 107 to provide electricity to the power-port of the device 5 which is configured to accept plug 104, which may be a USB plug or other type of plug. This type of power harvesting module may be well suited for re-charging devices such as digital cameras or MP3 players which are configured for obtaining power via their USB ports when plugged into a computer. The charger 99B may also supply power to a computer through USB plug 105 when this is provided from harvester module 62.

Figure 7C:
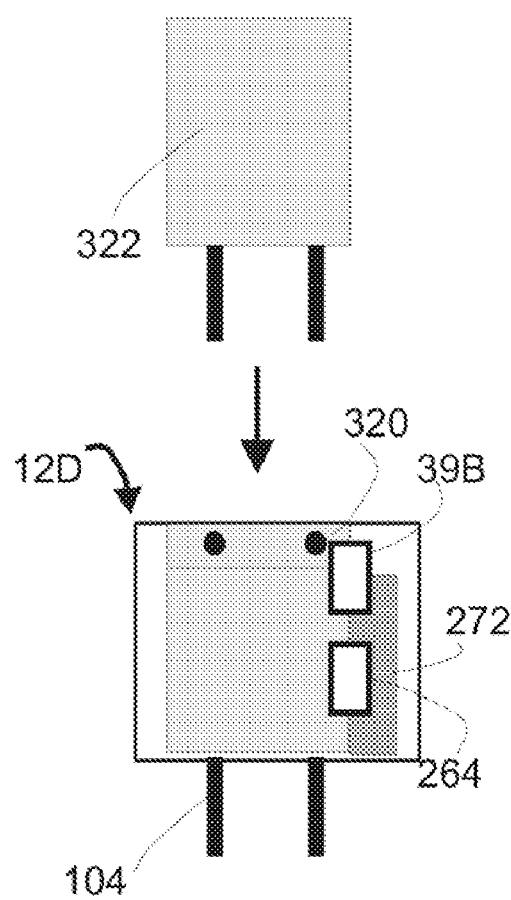
FIG. 7C illustrates transmitter configured to be plugged into an AC power outlet which supplies power not only to the transmitter but also to an accessory power outlet configured to receive the plug a device and to provide AC or DC power to this device. The transmitter is also configured with a power transmitter control PTC module.

In addition to using simple "wall plug" transmitters which are powered directly by standard AC sockets, other types of transmitters are also useful. In one preferred embodiment a wireless power transmitter is configured to transmit power as part of a wireless power network which also includes a remotely located device with a power receiver. The transmitter 12D illustrated in FIG. 7C is configured to be plugged into an AC power outlet which supplies power not only to the wireless-power transmitter 12D, but also to an accessory power outlet 320 which is configured to accept a plug 322 of a power cord of a wired-power-dependent device 6 and to provide AC power to this wired-power-dependent device 6. The transmitter is also configured with a power transmitter control PTC module 39B which controls an energy monitor 264 which allows the PTC 39B to monitor the AC power in order to sense data and timing signals that are transmitted on the AC power-line either from remote network components or from the wired-power-dependent device 6 which is plugged into the accessory power outlet 320. The wireless-power transmitter 12D is realized as a component of a mixed wireless-wired network which contains devices powered by both means. For example, if a computer is plugged into the accessory power outlet and it is turned on, then it may also send a signal over the power-cord so that the energy profile module 264 which can sense and process this signal to the power transmitter which is configured with an ambient. The signal can be used change the state of wireless-power operations such as initiating power transmission. In this example, a wireless keyboard can be powered only when the computer is turned on for use. If the computer then enters a sleep state, due to lack of activity above a selected amount, another signal can be sent to the wireless-power transmitter in order to stop wireless-power transmission. Other modules and features that have been described for with respect to the power transmitter (e.g., components of FIG. 1A and FIGS. 8A-B) can be added to this basic design.

Figure 7D:
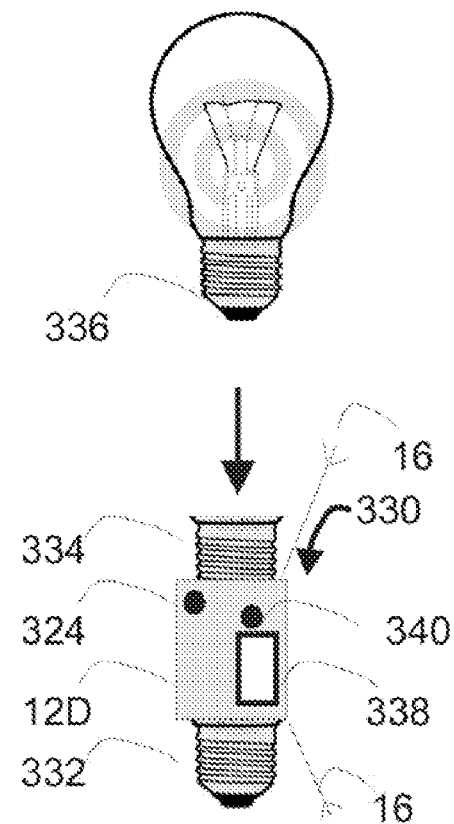
FIG. 7D illustrates a schematic diagram of a socket-transmitter which fits into conventional light socket outlet.

In an alternative preferred embodiment, a wireless power transmitter can be configured as a socket-transmitter 330, illustrated in FIG. 7D. In its most basic form, the socket-transmitter 330 includes a conductive contact 332 which fits into an outlet, such as a screw-cap for a conventional light socket outlet, and provides power to a wireless-power transmitter 12D which can transmit power. The socket outlet can be related to an incandescent bulb, a halogen bulb, or a different kind of bulb, as well as a track-connection for providing track-type lighting. The wireless-power transmitter can also have an accessory socket outlet 334 for accepting a light-bulb 336, so that powering the transmitter does not decrease the amount of light which is normally available from a bulb connected directly into a particular light-socket. The socket transmitter 330 may also include a control switch 338 which is at least one of: a manual switch for allowing users to manually control whether power is wirelessly transmitted or not; a remote-controlled switch for remotely controlling whether power is transmitted or not; and an AC monitor-controlled switch for controlling whether power is transmitted or not. The AC-monitor controlled switch can control power transmission based upon an on/off pattern of its power supply. In this last example, a user may flip a light switch on-and-off 3 times rapidly to start or stop the wireless power transmission. The socket transmitter 330 may also include a motion detector 340 for detecting motion and for automatically adjusting a transmission protocol in order to route wireless power transmission at least partially through an antenna 16 which has been designated to provide power in the region in which the motion occurred, as may occur using a directional antenna. The power transmitter can also contain an indicator-light 324 which emits a colored light at least periodically when power is being transmitted wirelessly from a position such as a recessed ceiling light. Especially if implemented in the form of a desktop light, or other light-source which is easily accessible (i.e. rather than a ceiling light), the bulb-type wireless power transmitter can have a power transmission antenna which can be manually adjusted by a user to transmit power primarily towards a particular direction. Manual adjustment of the transmitter or an antenna can serve to result in power being primarily transmitted across a particular area, and in a direction approximately defined by a horizontal angle. Alternatively, if the socket-type transmitter is located in the ceiling, then the transmission antenna can be remotely adjusted by a user to primarily transmit power to a particular area of a room. In a further embodiment the power transmitter can be implemented within the light-bulb itself having independent circuitry that primarily runs in parallel with the lighting function. The new LED based lights, can have a port which can accept the power transmitter. In this case the transmitter may reside adjacent to the light itself. Socket-based transmitters are advantageous since these provide good clearance for energy transmission compared to AC power outlets which are normally close to the floor and which may have their transmission paths physically blocked more often.

Different transmitters will provide different geometries of transmitted power fields as function of factors such as the antenna that are used, the shape of the room, various objects in the room which may be in the path of the transmitted power, etc. An accessory that can be used to place power receiver devices in improved positions for obtaining wireless power will increase the performance of a wireless power network, and assist in avoiding 'dead' or low power zones. Such a calibration device can provide visual indication signals each relating to a feature of a region of space in order to determine if these regions are active elements which form the functional spatial geometry of a wireless power field. In order to be considered part of the functional field of transmitted power, the active elements should meet a selected criterion such as containing at least a specified power level, or a power signal of a certain frequency, or a power signal containing at least two frequencies at specified levels, as well as other characteristics. The calibration device can provide a visual indication signal which adjusts the brightness of the signal as a function of the intensity the region in which it is located. The device can include a matrix of LEDs each of which are coupled to power harvesting modules, and each of which is capable of emitting light as a function of the power harvested and wherein the color of the light may be related to a different characteristic such as the frequency of the harvested signal. The matrix may be structured with rigid, flexible, or stretchable, structures which serve to maintain space between the individual power sensing elements of the calibration device.

The wireless-power transmitters disclosed herein may also be configured to periodically provide audible sounds or visual cues when transmission occurs; when transmission is halted, or when transmission occurs according to a specified protocol. Sensory alert signals may also be provided when the power being transmitted is above a particular level which may not be proper in certain environments or when humans are in the vicinity.

Figure 8A:
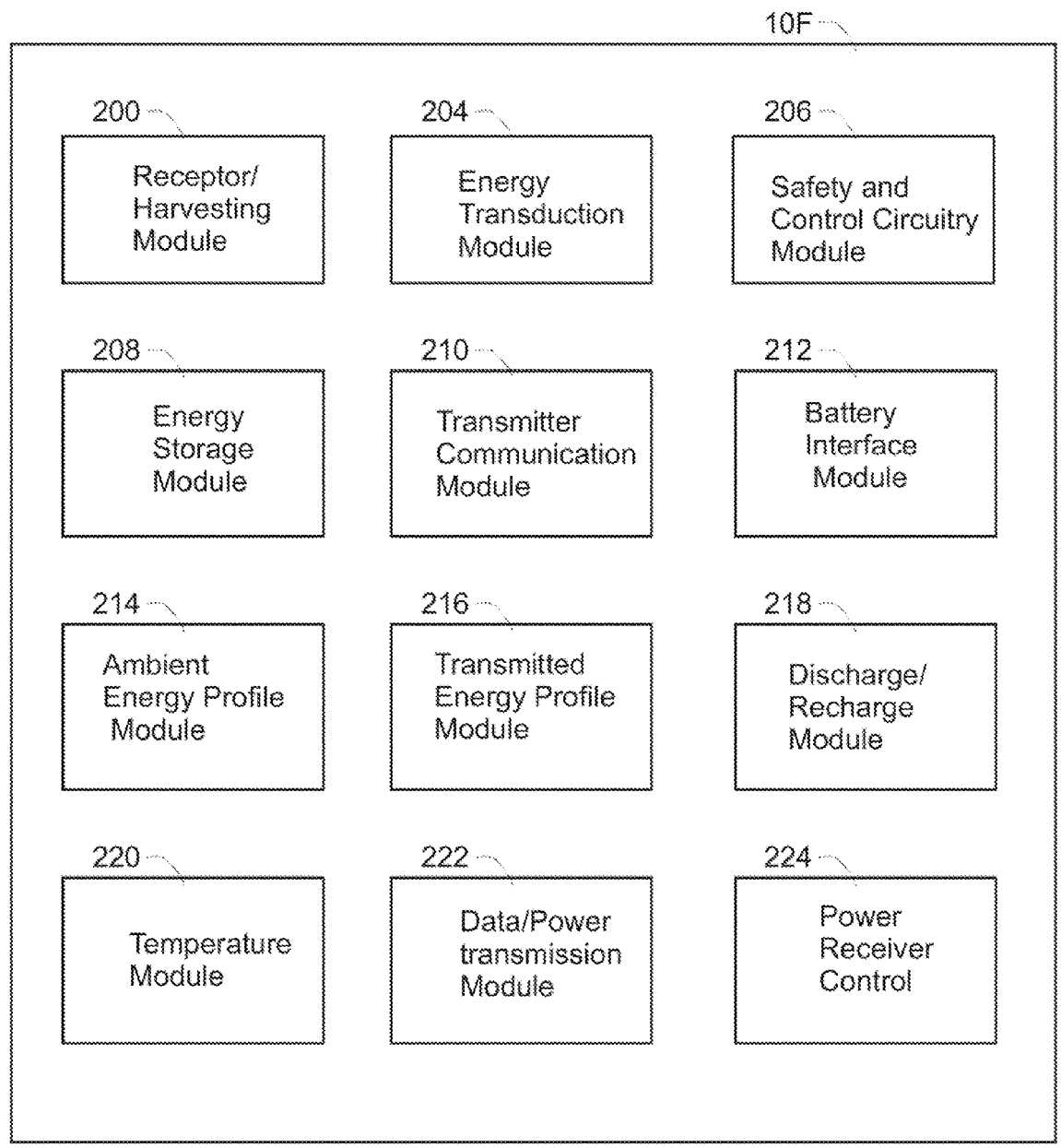
FIG. 8A illustrates a block diagram of example functional modules of a wireless harvester such as a wireless power-pack harvester device.
Figure 8B:
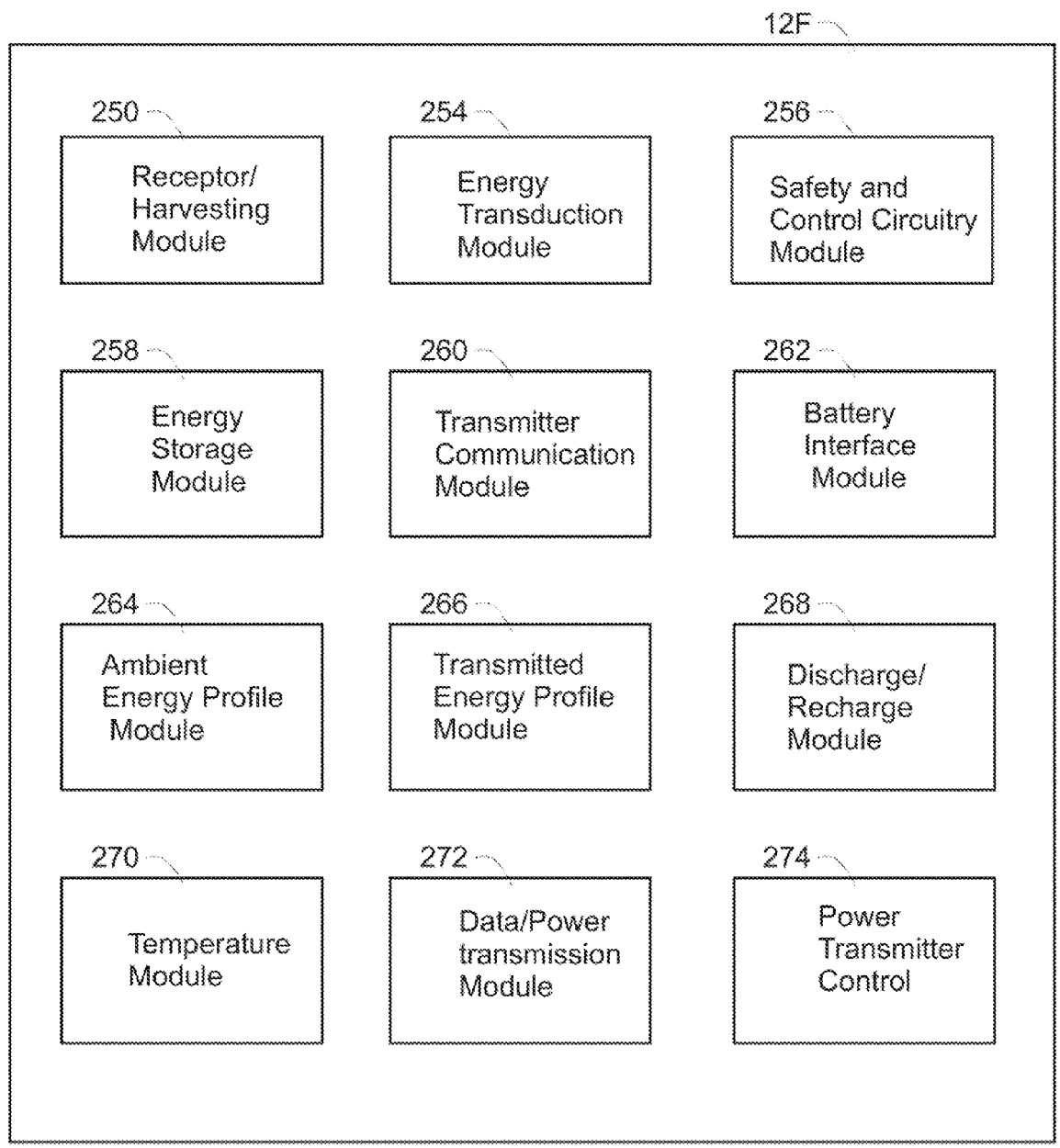
FIG. 8B illustrates a block diagram of example functional modules of a wireless transmitter device.

FIGS. 8A and 8B show a plurality of modules which can be contained in energy receivers 10, energy transmitters 12, or wireless-power accessories 90,99A/B which communicate or cooperate with components of a wireless power system. Only a portion of these modules may be utilized by any component of the wireless power system including a powered device 5,6. The following descriptions of the modules are not meant to be inclusive, and are meant to incorporate functions and features which have been disclosed in other parts of this application and which are reasonably similar to those referred to those specifically taught. The modules contain all hardware, software, circuitry, algorithms, and connections which are needed to provide the functionality of the module, and its cooperation with other modules. Although the modules are represented discretely, modules may share components and be realized as portions of other modules. More than one occurrence of the same module may exist in wireless power networks and within each device within the network, and further, modules do not have to exist within the housing of a single device.

FIG. 8A illustrates a block diagram of functional modules of a wireless power receiver device 10F.

The receptor/harvesting module 200 is configured for interfacing with at least one antenna and for controlling wireless harvesting circuitry related to harnessing of wireless energy. The receptor/harvesting module 200 may also be configured for obtaining energy from near-field power supplies.

The energy transduction module 204 is configured for converting wires energy into operational power and can contain circuitry for voltage regulation, rectification, and provides for sending of power to the energy storage module 208.

The safety and control circuitry module 206 is configured for monitoring power harvesting and ensuring that power generation remains within ranges which are selected to be safe both for a patient, if the power receiver device is used to power a medical device such as an implanted device, as well as for the device itself. Surge suppressors, capacitors, and other known power regulation circuitry may be utilized within this module. This module may also include circuitry for controlling visual and sound signals that may be provided to indicate to individuals the state or characteristics of wireless power transmission.

The energy storage module 208 is configured for storing harvested power and can include rechargeable batteries, capacitors, and control circuitry for controlling recharging and power supply operations it may also include thermal generators/monitors for controlling/monitoring/estimating temperature of energy storage components.

The transmitter-communication module 210 is configured for providing communication between the power receiver device and other devices of the wireless power network such as other power receivers and power transmitters. The transmitter-communication module 210 may be configured to transmit codes which identify the device to other parts of the network, and may include RFID technology circuitry for providing communication in more than one modality (e.g. sound, light, and RF energy signals). Transmission and reception of synchronization and timing signals is also achieved by this module.

The battery interface module 212 is configured for interfacing with standard rechargeable batteries, or specialized wireless battery designs, which the power receiver may act to recharge. The battery interface module 212 can also be controlled by a device 5 which is powered by the power receiver, such as a cell-phone device which can require more or less power during active and stand-by states. Circuitry may provide for monitoring charge, impedance, temperature, capacity, and other characteristics of the batteries.

The ambient energy profile module 214 is configured for sensing energy profiles of energy signals and computing energy measures such as dominant frequency, amplitude and phase, as well as statistical summaries of these measures. The ambient profile module 214 can also be configured to operate according to wireless calibration routines which serve to improve performance of wireless harvesting, and can assess ambient energy characteristics (which may include transmitted energy which is present in the local environment of the wireless harvester).

The transmitted energy profile module 216 is configured for sensing energy profiles of transmitted energy signals and computing transmitted energy measures such as frequency, amplitude and phase, as well as statistical summaries of these measures.

The discharge/recharge module 218 is configured for ensuring that the components of the energy storage module are discharged and recharged in order to intermittently provide 'exercise' to batteries and thereby increase their longevity and performance. Exercise may be scheduled to occur, for example, after a defined period of disuse of the device 5. For example, if a laptop is not used for a long time, the discharge/recharge module 218 can discharge the battery supply to a specified level, over a specified duration, and/or according to a discharge pattern, and then can recharge the device. The discharge/recharge module 218 is configurable by the user and may be disabled or forced to issue some type of visual or auditory alert prior to initiating an 'exercise cycle'. The module 218 may also be configured to detect the presence of a wireless power signal which meet selected criteria that promote that chance the power storage will be recharged to a sufficient extent after discharge. In another embodiment, the discharge/recharge module 218 uses the transmitter-communication module 210 to communicate to the transmitter and relay a request to initiate an exercise cycle and begins the exercise cycle only after receiving a confirmation signal that the transmitter will be on, or will turn on, at the end of the exercise cycle. When more than one battery is used by a device, each of the batteries is sequentially put through the exercise cycle or two or more may be exercised at the same time. Exercising may include: topping up the battery charge; draining the battery to create a shallow discharge; draining the battery to create a deep discharge; draining according to a linear function; draining according to an arbitrary function; adjusting the draining operation according to a temperature reading. During the exercise operation, after a first battery is drained it may be recharged in part by using the charge of a neighboring rechargeable battery instead of or in addition to using wireless transmitted energy. The discharge/recharge module 218 can contain circuitry for using Up the energy by operating a peltier circuit to upregulate or downregulate a battery, converting the power to light, activating wireless communication of power or data, or other means.

The temperature module 220 is configured for assessing temperature of modules and circuitry of the power receiver, especially of the rechargeable batteries, and for ensuring that temperature levels remain within a selected range. Further, the temperature module may be used to determine when, and if batteries are recharged, or can be used to determine if the temperature is within a range which has been defined as acceptable for providing power to a device such as an implanted device. In this manner, the powering the device and the recharging operations will not cause harm to a patient or to a device 5 that is receiving wireless power. The temperature module 200, can also be configured with heating and cooling devices which can ensure that components such as rechargeable batteries remain within temperature ranges defined for operational use and recharging to occur. For example, when the rechargeable power storage (and or the device which it powers) is located in outer-space, outdoors, under water, inside a mammal, or in other various environments active temperature regulation maybe required to ensure proper power cell longevity and performance.

The data/power transmission module 222 is configured for controlling data and power signals that may be transmitted by the power receiver device 10F. The module may also have a memory for storing information related to charging of the device such as power needs of the device, power-data transmission protocols which the device is configured for using, as well as factors such as age of a battery, number of charging lifecycles, time since last charge, resistance to certain temporal charge-patterns and other characteristics of a power which is provided. The module 222 is configured to derive, receive, and store, this type of information in order to provide improved power-data reception, supply, and efficiency. Mixed-network protocols, as well as data-only or power-only protocols, device priority settings, and other types of information related to providing data/power transmission functionality is achieved using this module.

The power receiver control module 224 is configured for controlling the operation of the other modules of the power receiver device in order for power harvesting, recharging, and supply operations and features to occur as intended. The power receiver control module 224 also ensures that the power harvesting device 10F works jointly with at least one wireless transmitter device 12F, as well as any other components of a wireless power network system.

FIG. 8B illustrates a block diagram of a plurality of functional modules of a wireless transmitter device 12F.

The receptor/harvesting module 250 is configured for interfacing with an antenna and controlling wireless harvesting circuitry related to harnessing of wireless energy within the power transmitter device. For example, a wireless power transmitter can be powered from a remote transmitter and can re-transmit the power in a similar or different manner than the original transmission.

The energy transduction module 254 is configured for converting AC or DC wired-energy into operational power and can contain circuitry for voltage regulation, rectification, conversion and provides for sending of power to the energy storage module 258 which can be used to store energy for intervals when the transmitter is not powered from wired sources.

The safety and control circuitry module 256 is configured for monitoring operations such as power transmission and modulates power transmission to ranges which are selected to be safe for the device itself and are within governmentally-regulated transmission guidelines. The safety and control circuitry module 256 can also supply AC or DC power to different parts of the power transmitter. If the transmitter 12F is used for transmitting wireless power to supply devices used for medical purposes, an alarm module may be included as part of the transmitter communication module 260 to warn that the transmitter has been "unplugged" or has otherwise experienced a functional failure.

The energy storage module 258 is configured for storing harvested power and can include rechargeable batteries, capacitors, and control circuitry for controlling recharging, and power supply operations it may also include thermal generators/monitors for controlling/monitoring temperature of energy storage components. This module may permit the transmitter to receive power intermittently, and the transmitter can be made into a portable device.

The transmitter-communication module 260 is configured for providing communication between the power transmitter device and other devices of the wireless power network such as other power receivers and power transmitters. The transmitter communication module 260 can contain alarm circuitry for providing alarm signals in both wired and wireless manners, including error signals and codes which are issued to notify of device malfunction.

The battery interface module 262 is configured for properly interfacing with standard rechargeable batteries to which the power receiver may send power. For example, the interface module 262, may contain protocols for transmitting power to different types of batteries. The power transmitter control 274 can access protocols of this module 262 when it receives signals from devices needing specific types of power to be transmitted for particular rechargeable battery types.

The ambient energy profile module 264 is configured for sensing energy profiles of ambient energy signals and computing ambient energy measures such as amplitude and phase, as well as statistical summaries of these measures. This module 264 can be assist in ensuring that transmitted energy either overlaps or does not overlap ambient energy which is present in the local environment, and may use more than antenna as well as antennae located in more than one location. This module 264 can also assist in detecting and decoding signals sent over the AC power-line.

The transmitted energy profile module 266 is configured for sensing energy profiles of transmitted energy signals, both of the power transmitter itself as well as additional neighboring transmitters with which it may, or may not communicate, using wireless or wired communication. The transmitted energy profile module 266 can compute energy profile measures for transmitted energy such as frequency, amplitude and phase, as well as statistical summaries of these measures. The transmitted energy profile module 266 can also assist in deriving power transmission strategies when the transmitter 12F is used a part of a wireless power network which provides power to a mobile device as it moves into different zones of the network.

The discharge/recharge module 268 is configured for ensuring that the components of the energy storage module 258 of the transmitter or those of receptor devices are discharged and recharged in order to 'exercise' the batteries and thereby increase longevity and performance. Exercise may be scheduled, for example, to occur after a defined period of disuse and may be accomplished by causing the transmitter to halt its power transmission and permit the battery of the wireless receiver device to discharge, after which power transmission can again be resumed.

The temperature module 270 is configured for assessing temperature of other modules of the power transmitter, especially the temperature of the rechargeable batteries 258 and transmission circuitry 272, and for ensuring that temperature levels remain within a selected range. The temperature module may be used to determine when and if batteries are recharged and may also be used to modulate their temperature.

The data/power transmission module 272 is configured for controlling data and power signals which are transmitted by the power transmitter device 12F, and controls which of at least one antennae are used during power transmission as well with various signals.

The power transmitter control module 274 is configured for controlling the operation of all the other modules of the power transmitter device 12F in order for power transmission harvesting, recharging, and supply operations and features to occur as intended within the wireless power system. The power transmitter control can also be controlled by a Master transmitter device, or may communicate control signals to other transmitters and this may occur in a wireless or wired fashion.

The transmitter can be configured to show, and allow adjustment of, the characteristics of the wireless power that is transmitted. In one embodiment, two mode-indicator lights can be provided on the wireless-power transmitter. One indicator signifies that the transmitter is operating in an automatic mode which uses a sensor such as a motion or wireless sensor to automatically turn wireless transmission on and off. The second indicator is lit when the wireless transmitter is chronically on. The two indicator lights can be the same color, or different colors, for example, green and red respectively. Only one indicator light, capable of multiple colors can also be used.

When the transmitter is in an automatic mode, movement can cause the device to transmit for a fixed amount of time such as 1 minute to 1 hour. This duration can be user configurable by way of hardware (e.g., via a nob-control) or by programming, using wired or wireless programming commands which are sent to the transmitter unit. The transmitter unit may also have a button which the user can press to provide a selected length of wireless transmission. The user can also operate a mode selector (physically or programmably) which determines one of 2 or more modes of wireless power transmission. A particular mode of transmission may entail adjustment of, for example, power transmission using particular frequencies and or level of power.

The transmitter may be hardwired, or may have physical controls which allow wireless power transmission programming. Alternatively, a software panel realized in a computer, PDA, or phone, or other programming device can be used for setting the transmission characteristics can be provided. Such a panel may display menu items such as:

Mode: Automatic On-always Schedule Manual User Configured.

In this example, selecting automatic mode causes sensors such as motion, light, or sound sensors to detect movement or requests for power transmission. Automatic-mode can also enable wired sensors, such as sensors which receive command signals over the power-line which powers the transmitter, or via a control line or wireless command sent from computer that operates wireless devices (e.g. a keyboard), or from a neighboring power transmitter. "On-always" sets the unit for chronic transmission. Schedule allows the user to set times for wireless transmission. Manual sets the transmission to only occur when the user pushes a button. User configured allows a user to customize a wire transmission strategy which is a combination of these other 4 modes. For example, from 9-5 the transmission may be always on, while from 6-8 wireless transmission is dictated automatically via sensors. Although the device can be in "schedule" mode, if a user depresses a button on the transmission unit, this can create a limited duration of, for example, one hour during which energy will be transmitted chronically, before reverting back to the schedule mode.

When selectable items are selected on the transmitter rather than in software, the transmitter may contain a physical knob which allows the user to select one of these 5 modes. A user configured mode can also be provided which can be a mixture of the other modes. This customized mode may have been previously loaded into firmware by the user.

Power-Data Communication Protocols

Figure 9A:
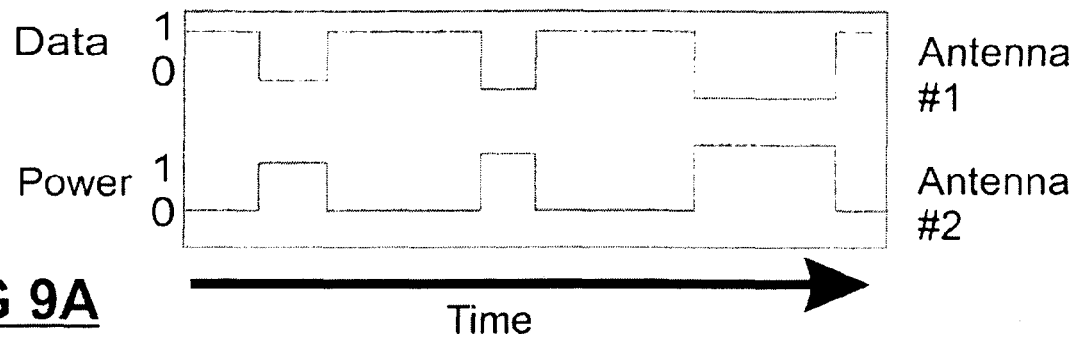
FIG. 9A-9D illustrates charts of transmission schedules for power and data transmission.
Figure 9B:
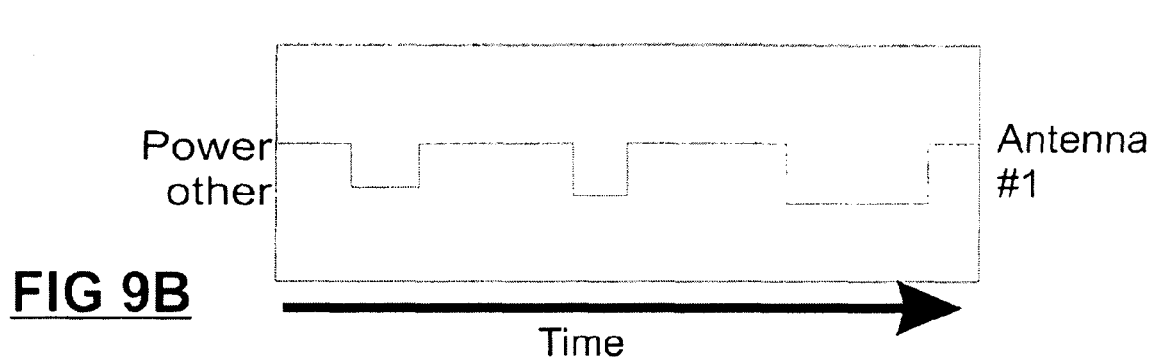
Figure 9C:
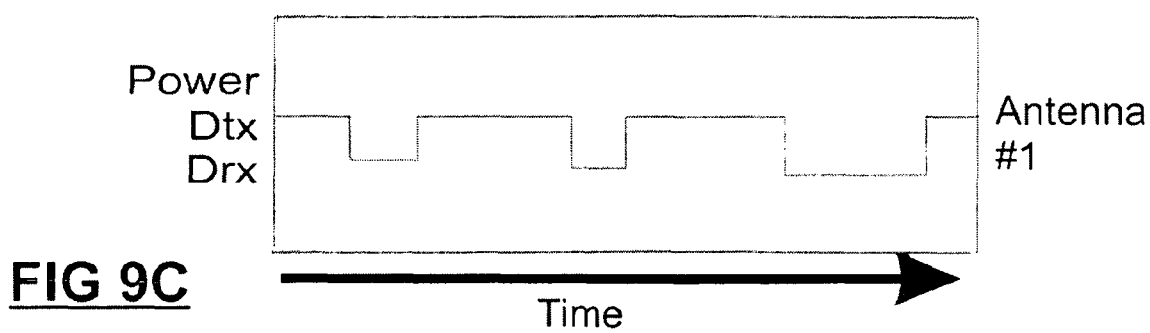
Figure 9D:
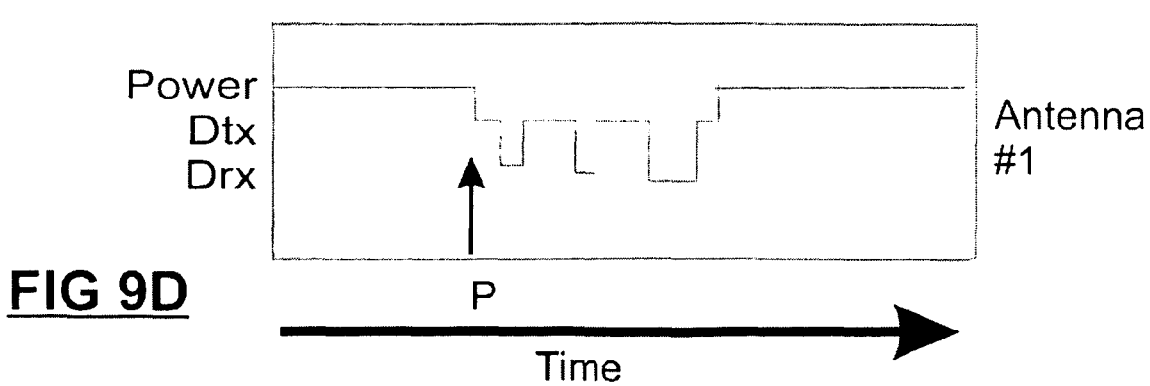

FIG. 9A illustrates activity charts of transmission schedules for power and data transmission. Power and data transmission may be provided simultaneously or not, as required in relation to different applications. For example, if there is any risk that spectral characteristics of signals used for data and power transmission may overlap, or interfere with each other, then data and power transmission operations may be accomplished in manners which decrease this risk of overlap or interference. The chart in the first panel shows the temporal schedule for communication of data and power signals. When the data value is set to '0' (i.e. false) then data communication is halted, while a value of '1' (i.e. true) indicates data operations can occur. The function for data is opposite to that shown for power, indicating that the two types of operations are scheduled to occur at different intervals which are non-overlapping. The power transmission intervals and data transmission intervals may be the same duration, different durations, or may be set dynamically according to the needs of the components of the wireless network or according to times such as time of day. The data and power signals can utilize the same antenna or two different antennae as shown in FIGS. 2A-2E. FIG. 9B shows a similar chart and reflects what might occur when a single antenna is used for communication of several different types of signals including those received and those sent. FIG. 9C shows a similar chart and reflects what might occur when a signal antenna is used for communication of clearly defined types of signals including data which is received (Drx) and sent (Dtx). Rather than alternating between two types of data communication the protocol may alternate between power transmission and two-way data communication. FIG. 9D shows a similar chart and reflects what might occur when a single antenna is used for communication of different types of signals. In this case, wireless operations share time which is used for transmission, data reception, and data transmission. In the figure, since different types of data is received the graph for (Drx) operations is not all aligned with respect to its y-value, indicating different devices are receiving information or different types of data are being communicated in a sequential fashion. The intervals can be defined in a default operating protocol stored in the memory of each of the components of the wireless system. The type of communication can also be fully or partially 'event based'. As such the type of wireless operation which occurs can be determined by an event, such as the occurrence of patient input ('P' in the figure) using a controller device. Patient input, which is provided by a patient can be received by a component of the wireless system during a default data receive mode of any of the components of the wireless system. The reception of a signal that an event has occurred can trigger an 'event protocol' that causes data to be sent and received by at least one component of the wireless system for a specific period an according to the schedule defined in the event protocol, after which a default protocol (e.g., alternating power transmission, data transmission, data reception) again is established. Although the mixed-network data/power strategy may be realized with only one or two antennae by any particular device, different operations represented by the graphed functions may entail functionally connecting or operating at least one from a set of antennae to achieve either transmission or reception of power, or data, (or communication related to timing, energy profiling, energy sensing, and multi-device synchronization operations). In other words, different types of operations may utilize different antennae, or sets of antennae, and may cause re-allocation of sets of antennae to achieve particular operations. Additionally, different operations may activate various filtering circuits in order to isolate the electrical interference which can occur when power-related operations and non-power related operations occur with some overlap or in close temporal proximity. In one embodiment, the wireless system can contain at least one power transmitter device 12F configured for operating to provide power transmission and two way data communication according to a default protocol, at least one power receiver device 10F configured for receiving power and data communication; at least one transmitter communication module 210 which is configured for providing an event trigger signal based upon at least one of an event trigger issued by the power receiver control 274 and an event trigger provided by patient input to a device 5, such as a patient interface controller; wherein the power transmitter device 12F is configured for operating according to at least one event protocol when it receives an event trigger signal while operating to provide data communication. Since the power transmitter device 12F may not operate to permit communication when the event trigger signal is sent, the power receiver device 10F is configured to provide this signal for a duration defined as sufficient for the power transmitter device 12F to again provide communication. Synchronous, a-synchronous, event-based power and communication protocols, as well as mixtures of each of these may be used in different situations by a wireless data-power network.

Priority-Based Power-Data Communication Protocols

Use of at least one type of Power-Data Communication Protocol (PDCP) becomes even more important when multiple devices of a wireless network exchange power and data in a wireless manner. Several PDCPs are disclosed, each of which can be used separately or which can be combined (and which may have overlapping intervals and features). The PDCPs can be relied upon at different times, in response to different events, and according to the state of the network (number of devices, power/data needs of the devices, etc) in order to provide power and/or data transmission in a manner which allows the wireless network to function successfully. Although a majority of data and power communication may occur in a wireless fashion, particular components of a network can have wired connection, for example, as may exist between a specialized wireless network control card used by a laptop and a plurality of power transmitter devices.

A 'tiered receiver' PDCP can be implemented when there is one transmitter and at least two receivers. In one embodiment, one of the receivers has a higher priority level than the other with respect to requesting, selecting, or modifying at least data or power communication operations of the system. In another embodiment, priority can be allocated to different receivers at different times, in response to the occurrence of an event, or as a function of the network state.

A 'tiered transmitter' PDCP can be implemented when there are at least two transmitters and at least one receiver. In one embodiment, one of the transmitters has a higher priority level than the other with respect to requesting, selecting, or modifying at least data or power communication operations of the wireless network system. For instance if a first transmitter has a higher priority value than a second transmitter then the first may designated a "master" transmitter, while the other transmitters are "slaves". This embodiment is usefully implemented when the master transmitter can access a clock signal and is also configured to transmit power only during certain times of day, and is further configured to turn off all slave transmitters so that their transmission operations also confer to this schedule. This lead to advantages such as using less power. In another embodiment, a priority (control) value can be allocated to different transmitters at different times, in response to the occurrence of an event, or as a function of the network state. For example, if each transmitter has a motion detector and one senses motion then the respective transmitter can assume, or be assigned, a higher priority value and may become the master transmitter. This transmitter is then allowed to communicate "orders" to the slave transmitter such as initiating leaving a 'lower power' state and transmitting according to a selected protocol. Further, the slave transmitters may be instructed or configured to intermittently send data if motion is detected or stop transmitting after a specified duration if it is not detected during that duration.

A 'tiered transmitter-receiver' PDCP can be implemented when there are at least two transmitters and at least two receivers in a wireless network system. In one embodiment, one of the receivers has a higher priority level than the other with respect to requesting, selecting, or modifying at least data or power communication operations of the system. In another embodiment, one of the transmitters has a higher priority level than the other with respect to requesting, selecting, or modifying at least data or power communication operations of the system. In a further embodiment, a transmitter or receiver may have priority over all other transmitters and receivers on the wireless power-data network system. In another embodiment, priority can be allocated to different transmitters or receivers at different times, in response to the occurrence of an event, or as a function of the network state.

A 'tiered transmitter-receiver-device' PDCP embodiment can further be implemented when the network includes accessory devices which are neither transmitters, nor receivers, but rather are devices which communicate with these. Accessory devices can also obtain priority values within the network system. For example, in the case of an implanted medical device which communicates with an external patient programmer, if the programmer needs to send the implanted device a command it may send a request signal (e.g., an event signal having priority) for power transmission to be stopped from all power transmitter modules, during data communication operations. In this case a first component of the mixed-network determines that data communication is needed between it and a second component of the mixed-network and it sends a stop transmission of power request signal to all power transmitter modules which stops power transmission for at least a selected duration of time. In another case, if an implanted device (which can include a wireless power receiver) has issued an alert signal in response to a detected event, such as epileptiform activity, and needs to provide stimulation therapy to the patient, then it may also send an event signal which is a request for halting power transmission and/or data transmission. This event trigger signal would hold priority over other scheduled programs of power/data transmission defined by an existing operational protocol.

A 'fixed-priority' PDCP embodiment can be implemented in which selected times or intervals are defined for data and/or power communication, or where devices of the network simply have constant priority values. FIGS. 9A-9C graphically show protocols that lend themselves to 'fixed-priority' PDCPs. One example of this type of PDCP comprises the periodic occurrence of a 30 second power transmission interval which is followed by a 10-second data transmission interval. The data transmission interval may comprise bi-directional communication or may contain a 5-second interval of power-receiver-to-power-transmitter communication, followed by a 5-second interval where the direction of communication is reversed. The data transmission interval, can also serially include providing a communication interval for each device in the network (in descending order of priority values assigned to each device) in order to avoid confusion of data streams from devices in the network. Alternatively, power may be transmitted between the hours of 1 a.m. and 8 a.m. every day, but not outside of this range, which is defined within the network as a data communication interval. Another example of a fixed-priority PDCP is a system in which a selected transmitter always serves as a master device that operates according to a fixed protocol or which otherwise determines the power/data communication operations of the rest of the components of the network.

A 'dynamic priority' PDCP embodiment can be implemented in which devices of the network are allowed to make requests for priority, and priority values which are assigned to different devices can thereby change over time depending upon the operations, events, and states of the network. When a device has top priority it may allow, delay, or reject a request for priority from other components of the network, it may also request that the device ask again after a specified interval.

A 'time-constant priority' PDCP embodiment can be implemented in which communication related to data and power have priority at different times.

A 'time-dynamic priority' PDCP embodiment can be implemented in which times for data and power communication occur in a dynamic manner. For example, times may be allocated to data or power communication, or allocated for operations specific to a particular device in the network in a dynamic manner. For example, priority for a operation can be allocated depending upon state of network. There may be defined a "post-event" network state where an operation such as data communication has priority, compared to a 'standard state' or 'default state' in which the network mainly accomplishes the wireless transmission of power.

A 'fixed-priority' PDCP embodiment can be implemented in a fixed state network. Fixed state networks operate according to a constant rule set. Priority may be requested and returned by a device, or sequentially requested by multiple devices, but the protocols do not change.

A 'fixed-priority' PDCP embodiment can be implemented in which Tiered state network. Tiered state networks operate according to a varying rule sets. Rules for attaining how priority may be requested and returned by a device can change depending upon the state of a network, and priority may be assigned to devices related to the state and during sequential requests by multiple devices, control is made dependent based upon this priority. For example, a data or power priority state may occur in which priority is given to data or power operations, respectively.

In the case where transmission of power was interrupted for an extended period of time, and power levels are low, then transmission/reception of power may take priority over (most) data transmissions. For example, power may have priority over data when:
  a. a scheduled event does not have enough power to be accomplished;
  b. calculations about a scheduled event predict that the event will cause a drop in power to go below a selected minimum value;
  c. power has dropped below a selected minimum value; and,
  d. a device has stopped communicating data in a manner which has been defined as a data transmission failure event.

Alternatively, during the occurrence of a data-critical task, then power transmission operations may be halted or delayed. For example, power transmission may be trumped by data related transmissions if a wireless device is a medical device (or an external patient controller device) which has done at least one of the following:
  a. issued an alert signal;
  b. initiated a period of sensing of bio-logical data;
  c. detected an abnormal medical event;
  d. detected an abnormal medical event within a recently defined period;
  e. initiated a therapy such as cardiac or neural stimulation;
  f. initiated transmission of a data record;
  g. initiated a calibration routine;
  h. delayed data transmission for a selected maximum period during power transmissions;
  i. initiated an operation defined as having priority over power operations; and,
  j. initiated an operation defined as having a higher priority value over currently pending power operations having lower priority values
  k. detected the occurrence patient input event in which the patient has initiated an operation which is associated with a data over power preference.

The PDCPs can be used with systems which are designed to transmit power using a first frequency range and data using a second frequency range, or when power and data are transmitted using a first frequency range, where data is transmitted using modulation or pulsing of the power carrier signal. Additionally, the PDCP can not only determine if power or data are restricted to certain times, but also can contain parameters which dictate how particular antennas are used. For example, two antenna can normally be used to obtain power signals, and if an interrupt signal is obtained which contains a request for data transmission (which has a higher priority value than the current power operations) then one of the two antennae can be reallocated to data transmission operations, rather than requiring both antennae to be assigned to handle the data transmission.

Similar to internet protocols which relate only to data transmissions, the PDCP's can comprise formats which enable handshaking to occur. For example, an interrupt request sent by a module of a network may be formatted to contain the following information: module identification number; priority value of request; duration of request; interruptible; request type; qualifier #1; checksum info. The module identification number identifies the module of at least one module which exists in the network and may also identify if it is a transmitter or receiver module. The priority value of the request is a value which is programmable and which can be compared to the priority values of current or pending operations in order to determine how it will be processed (e.g., rejected, accepted, queued). The duration of the request can be given which tells the other modules how long it will need to operate if the event is allowed (this may also be blank if not known). Interruptible is a parameter that relates to whether, once started the process is allowed to be interrupted (this may also have a value which can be set so that if other operations with priority values above a selected value occur, then these can interrupt the proposed operation). Request type can relate to whether this is a data or power transmission operation, and whether it is requesting partial, or full, allocation of receiving or transmitting antennae. Qualifier #1 can include fields of additional information which can used in a programmable fashion, and which can be stored, and may include error messages, systems checks, system calibration parameter values such as constants, and the like. Checksum info can be included and can contain data and integrity checks as well as beginning and end of transmission codes. Checksum info can also contain timing pulses or timing information which can be used to ensure that two or more modules of a wireless system remain synchronized. Even in the case where clocks differ, the timing pulses can be used to create adjustment coefficients in order to reestablish synchronized operation. This is important when fixed or time-constant protocols are used when data and power are only transmitted at discretely defined intervals.

'Resource based protocols' can also be provided. One example of such a protocol occurs when a patient wears a portable energy transmitter, which may be configured with an antenna in order to efficiently transmit RF energy to an implanted device, and which may also use an antenna for improved energy reception. The portable energy transmitter PT1 12a can sense local fields of signal energies S2 which are transmitted from a remote power transmitter, and can complement or supplement this energy S2 with its own transmitted energy S4 if the transmitted energy S2 does not meet a criteria such as being above a selected level and further not occurring above this level for a specified period. The portable energy transmitter may also be powered by energy signal S2 of the remote transmitter (and or can only use its own battery), but can obtain better signal strength than an implanted device and thus usually harvest energy more efficiently. In this manner, the portable energy transmitter can supplement the signal S2 with its own transmitted energy S4, and further serve as an "amplifier" or "relay" for remotely transmitted energy S2 by harvesting it (and possibly storing it), and then re-transmitting it. When an external patient device is used in addition to an implantable device, these two devices may be powered from two different transmitted signals S2a, S2b in order to decrease the risk of one device effectively shadowing the reception of the other device. Further, since lower frequency signals can be transmitted into the patient's body better than high frequency signals, while higher frequency signals can require smaller harvesting antennae and be better suited for sending energy to external devices.

The above described protocols can be implemented by protocols which are initiated from an external patient controller device (EXD). The EXD can have features such as those described in co-pending U.S. application Ser. No. 11/710,902 entitled "Systems and methods of medical monitoring according to patient-state". As such, the EXD can provide the patient with alarms related to power usage and recharging and obtain patient input which guides the operation of the wireless power system in response to the patient input. For example, the patient may use the EXD to start, stop, increase, decrease, or otherwise adjust the power transmission operations of the transmitter and power harvesting operations of the receiver. The EXD may automatically issue 'power transmission start' and 'power transmission stop' commands which activate or deactivate one or more transmitters according to a time of day, an operation which is to be carried out by the implanted device, a recent history of power harvesting, a patient environment (e.g., the patient will be entering an environment with unique power signatures which may be related to security scanning or medical testing) or in response to patient input. The EXD can also issue commands, and/or requests for approval, to both power transmitters and implanted components that acutely change the state of the components of the wireless power network such as 'power transmission start for 30 seconds', 'power transmission stop for 30 seconds', 'change to preferred power transmission protocol #2', 'enter low-power state', 'enter high-power state'. The EXD can also be configured to work with sensors in a patient's home to enable power transmitters to adjust their transmission characteristics based upon the location of the patient so as to optimize energy transmission. Calibration and adjustment for different clocks which reside within external and implanted devices may also occur under the control of the EXD, which can also transmit wireless clock signals to assist in synchronizing operations of these devices.

Powerless Calibration Using Device Codes, Automatic Indexing and Other Manners

Wireless power networks in both public and private settings should be able to provide power to an ever expanding set of new devices. Individual devices may have different protocols for wireless communication of power and/or data, and the wireless transmitters should be able to adapt to these protocols. In an illustrative example the wireless transmitter component is realized in the form of a device which is a computer accessory. As a user introduces each new device into the wireless network environment the power transmitter should be able to accommodate the data/power transmission protocol required by the new device. Several methods may be implemented, each having several variations that may be used to ensure proper network function. The first step to identify the device to the wireless power network as may occur by: having the device issue a protocol signal to the network which indicates the type of wireless protocol which it expects; having the device issue a protocol signal to the network which indicates the actual parameters of the wireless protocol which it expects; having the user manually configure the protocol using a software program; having the user manually configure the protocol using a physical device such as a CD, Flash-memory device, or other accessory which contains the protocol information. The second step is to select or adjust the wireless protocol and configure at least one transmitter of the wireless power network to achieve this wireless protocol as may occur by: adjusting the power/data communication protocol according to a signal received from the device based on the protocol type; adjusting the power/data communication protocol according to a signal received from the device based on the protocol parameters provided by the device; and, via 'automatic indexing' achieved by adjusting the power/data communication protocol according to a signal received from the device based on the protocol type, and further, obtaining the correct protocol from computer memory or by using the internet to access a pre-defined website which hosts this information and which can communicate with the wireless power network. Further, when the wireless network is managed by a computer, a user may be able to select protocols for different devices, select which devices have the highest priority for power/data communication, and resolve device conflicts, when certain devices do not work well when powered by the same network. In one example, a wireless keyboard is purchased by a user. When the user returns home the device emits an 'identification code' signal to the wireless network such as 'A1432'. The wireless power transmitter receives this code and transmits it through the USB into the computer where software then automatically uses the internet to lookup the wireless protocol for an 'A1432' device, so that it may communicate power/data to the device at least a portion of the time. This type of 'identification code' can be used to quickly identify new devices to wireless networks, to power-pads, and the like in order to customize the operation of these wireless transmitters.

Wireless System Calibration, Timing, and Communication

Similar to electrical transformers, the transmission or harvesting components of wireless system can include electronic or physical switches which toggle operation for either 50 Hz or 60 Hz environments. For example, system components can transmit or receive energy at either 50 Hz or 60 Hz, and can also use either frequency as a timing signal (rather than requiring an internal clock). Alternatively, components of the system can transmit at submultiples or multiples of the mains energy, so that a 5 or 10 Hz signal is generated by being triggered by every 10 (12), or 5 (6), cycles of the power-line energy waveform. Wireless power can be adjusted in relation to harmonics of the power-line frequency, for example, 300 Hz may be obtained by operating upon every ⅙ (or ⅕) segment of the wavelength of the AC power source. Setting a start-time using the maximum or minimum of the mains-line energy can subsequently enable synchronization of events at faster than 1/60 sec since the error of the time chosen for maximum voltage should be much less than that. Utilization of mains energy as a calibration signal is useful for synchronization and timing purposes when multiple transmitters are implemented, since this can occur without requiring as much communication between the devices (e.g. without one device sending a trigger related to a particular phase value). By setting the phase of the transmitted signal relative to the phase of a peak of the 60 Hz signal, the need for sending timing synchronization pulses between transmitters can be fully obviated. For example, a first transmitter can synchronize to peak of the 60 Hz signal, and the second transmitter can shift the phase of the transmitted signal, one or more times, in order to attempt to increase power reception via improved summation of the signals.

When the wireless power system contains a plurality of components (e.g., multiple power transmitters and/or power relays and/or controllers which control and coordinate activity of system components), a portion of which can be plugged into wall outlets, then inter-component communication can occur over the mains-line itself. For example, using a home's existing electrical wiring (or existing Ethernet, coaxial, USB, Firewire, optical, or other 'wire-based' networks), communication can occur via Ethernet or other communication protocol (for example, using a PowerLine HD Ethernet Adapter selected to be the DHP-300 from D-Link). This strategy facilitates wired communication of timing and data signals between wireless system components. Wired communication can be useful in applications for which a mobile device is transported throughout a structure such as a home or factory. For example, information about successful wireless power transmission can be relayed from transmitter to transmitter as the device moves into the zones of different transmitters. Although transmission of power and data has been realized within wireless systems using multiple modalities (e.g., radiowaves, light, laser, and ultrasound), so that the power/data transmission occurs without issues of destructive interference, wired embodiments can offer advantages. Use of the power-line for providing timing and data communication between several power/data transmitters is an advantage of the current invention. Either the AC signal itself, or signals sent using the physical wires used to transmit the mains power AC within a building can be used to adjust the power and data transmission characteristics of signals transmitted by the transmitters, and can be used to synchronize components of the wireless network. This type of physical connection can serve to provide redundant data communication (where wireless and wired communication occur approximately simultaneously) or a backup/secondary type of communication when a first type, such as wireless data communication fails. Further, if solely relied upon, the 'wired' communication can act to reduce power, heat, and cost associated with wireless transmission of both power and data when these require separate antennae. In certain environments, such as medical wards, a 'wired' communication may be required by law or policy.

In one embodiment, the present invention relates to wireless power and communication systems, and more particularly to a 'mixed network' which includes both power-line and wireless communication of both power and data. A mixed network may include a 'network controller' and at least one 'network node' allowing remote-based wireless access/transmission with various wireless devices. Data and power can be relayed using existing power lines, wireless means, or both. The network nodes may provide wireless power and data communication to wireless devices while the power lines provide communication between the network nodes and at least one network controller which may be connected to a wireless transmitter (which may also be able to wirelessly transmit data). The network controller manages communication between itself and remotely located network nodes, for example, by sending commands, calibration, synchronization data, error messages, and other types of data which may normally occur in a network. Two way data communication is possible if the nodes also transmit data back to the network controller. Additionally, data may be coded so that when it is transmitted along the power-line, it is received only by the node for which it was intended. Data may be communicated over a power line, and/or wirelessly, in a manner which is redundant, and approximately simultaneous or sequential. Data may also include information relating to encryption, handshaking, wireless power transmission, device information, node location, node identification, priority requests and assignments related to prioritizing network operations, access passwords and control signals related to users, devices, and nodes accessing the mixed network.

The mixed network architecture is preferably realized by utilizing sections of existing power-line infrastructure of residential or commercial sites it may also use alternative 'line-based' media such as internet (e.g. fiber optic, Ethernet cable, coaxial cable). The mixed network may relay data along paths which provide both power and data, such as the power-line, or when optical cables are used for data then power may be provided by the power-line, with no data component being transmitted along that path.

Network 'relay nodes' may block access of data communication along a particular path of the power-line grid in order to provide secure and private communication within sections of the network which may be defined as a particular room, building, or set of structures. Relay nodes may also be used to prevent distortion of communication signals leakage of signals through power outlets which are not involved in the operation of the mixed network. Network 'relay nodes' may also provide filtering, amplification, attenuation, or other signal processing of the data which is being transmitted along the power-line infrastructure. 'Relay nodes' may also receive data from one part of the network and send the data along other paths of the network, while not sending the data along other paths (traffic control functions). This can be used in to decrease system nodes from receiving data meant for other nodes. This can also be used to define 'active' zones, such as those which may exist in a security or alarm system.

The mixed network may use network nodes to provide remote devices with wireless power and data to achieve internet access, mobile telephone operation, streaming media, surveillance, and other functionality and this may occur as a function of floor, apartment, room, or section of a structure, which may also be defined for public areas (e.g. train-car, airplane seat, table of a restaurant, elevator etc). A 'data link' is formed between two components of the network which communicate using at least one communication medium. Some network nodes provide communication between the controller and devices using such protocols as: IP network protocol (IP); packet routing; signal processing; and modulation/demodulation, handshaking, and other protocols as are known. Protocols may include routines which encode, encrypt, modulate, demodulate, decrypt, and decode data signals.

Calibration and adjustment related to sending and receiving signals can improve system performance. In one method the first step includes sending a signal that a calibration routine will be initiated, the second step includes send a calibration sequence (e.g. a transmission of calibration signals having sequential phase values, 1, 2, 3, and 4), the third step is to obtain the results of the calibration (e.g. the receiver device transmits results to the transmission device), and the last step is to derive the optimum setting based upon the test results. For example, a sine-wave function may be fit to the power levels derived by the calibration routine in order to derive the optimum phase.

However, a calibration routine may not remain useful if a device, such as a computer keyboard is moved to a different location. There are several strategies for creation of 'calibration triggers', which are events which cause a calibration routine to be evoked. For example, if a drop in power reception by the receiving device (e.g. which powers a keyboard) occurs, this may lead to a 'calibration trigger'. The drop may be below a specified level which is required for usefully charging the device, whereas a drop which decreases power harvesting from 'excellent' to 'good', rather than from 'excellent' to 'poor' may not trigger a recalibration routine. Rather than simply being applied to phase, the calibration routine can be applied to the (relative) frequency, direction, transmission antenna, PTU, spectral range, waveshape, strength, or other characteristic of the transmitted signal. It is a particularly important aspect that the calibration routine may be programmed to select the characteristic which is tested in a particular order, for example, first phase may be iteratively adjusted, and if this calibration process does not yield a desired result then the next characteristic, such as frequency of the transmitted signal is adjusted and evaluated. Particular devices, transmitters, and systems can use unique calibration routines which may be stored in the hardware of the system (e.g. within ROM of a power transmitter). The PR may transmit feedback signals related to different characteristics (e.g. level of power) of the energy signals which are received during the calibration routine, or may only send a feedback signal when power reception above a specified level is restored. Further, the calibration procedure can be accomplished, either approximately only within the receiving unit, within the power transmitter, or in both devices and may further require collaboration of the devices.

Another strategy relies upon antenna calibration by the power harvester, or power transmitter, or both. The simplest case may be simply calibration by the power harvester. The harvester may be configured with two, or more, antennae which are preferably maximally orthogonally disposed to each other. These can be configured to capture transmitted or ambient energy which arrives primarily from at least one particular direction. These antennae can be connected to one or more harvesting circuits. When connected to a single harvesting circuit, the circuit can select which subset of the antennae are used for harvesting, for example as may occur from time to time, according to a button-press of a user, expiration of a 'wait period', due to a signal sent by one or more power transmitters, or due to a drop in energy harvesting below a certain level or above a certain proportion. In this manner, the maximum orientation of the received energy can be adjusted in steps of approximately 20 degrees or more. Alternatively, rather than using equal increments, a binary search strategy may be used (e.g. cut total by half, then half of that half, etc). The maximum power reception may occur when the transmitted energy and receiving antennae have polarities which are aligned. Rather than adjusting the orientation of the antennae, a user may assist in increasing power harvesting by reorienting the harvesting device itself. In this case, an audio signal can be configured to change volume when device is rotated, as a function of how much energy is received. In some instances, an audio or visual signal may be emitted from the wireless harvesting circuit, while in others the signal may be configured to issue from a cell-phone's speakerphone, a computer's speaker, or by a speaker of any other device which is powered by the power receiver module.

When the transmission of power is not needed, or desired, this can result in an undesired wasting of energy or other unwanted effects. Several strategies can be used to avoid this unwanted effect:

a. devices which rely upon wireless power can be configured to send 'deactivation' signals when these are deactivated by a user. For example, part of a computer going into 'sleep mode', the activation of its screensaver, or being 'shut down' can include the operation of sending a signal to the wireless transmitter to halt operation;

b. The wireless power system can be configured with a motion sensor which halts transmission of power when motion is not measured for a selected interval;

c. The wireless power system can be configured with a light sensor which halts transmission of power after the lights in the room remain off for a selected interval. This may be particularly useful when wireless power is used in office environments;

d. The wireless power system can be configured to sense the electrical load on a circuit, such as a circuit which powers a computer and halts transmission of power when wired power usage is not measured for a selected interval;

e. A wireless device can be configured with a circuit or routine which sends a signal to the wireless transmitter when it is connected to a physical link and does not need wireless power. In the case of a laptop, if the user plugs it in then it can transmit a 'deactivation' signal to a dedicated power transmitter which normally supplies it with power;

f. The wireless transmitter can be programmed to periodically transmit a 'device query' signal which must be responded to by a power harvesting device emitting a 'device present', or 'device has low power', for power transmission to continue, or to be restarted in the case where power transmission has stopped. Wireless power harvesting devices may send 'device has low power' or other signals independently, rather than simply in response to a 'device query' signal;

g. The power transmission device can contain a real-time clock and can be programmed to transmit power according to a defined schedule; and, h. The power transmitter can send power during a 'test' interval. The receiving device can determine how much power was received as well as determine its power requirements and can transmit a request to the power transmitter to intermittently transmit power according to a particular schedule and at a particular level. Power transmission therefore occurs according to provide 'calibrated consumption'.

These strategies can be programmably implemented within the power system, and multiple strategies can be relied upon in a concurrent or sequential manner, which may be under control of the user, or which may be dictated by the setting (e.g. emergency room) in which the wireless transmission is to occur. Further the transmission protocol can include priority with respect to how to handle situations where simultaneously active protocols yield conflicting results. For example, if the lights in a room are off, and power transmission has been cancelled (according to 'c'), it may be resumed if a ('device has low power' signal is sent from a local device according to 'f').

Improving Performance and Longevity of Wireless Power Supplies

When the wireless power supply is not used much, any rechargeable batteries that work with a device 5 may experience decreased performance and longevity. When there is a finite amount of charge held by a battery, de-charging the battery will simply shorten its life and utility. However with wireless power methods, a rechargeable battery can be discharged and then recharged, for example, in order to provide exercise.

In one embodiment a device using the rechargeable-power supply device 60 can have a discharge/recharge module 218 which automatically schedules discharging when the device has not been used for a while. In one example, the device can cause the rechargeable batteries to periodically fully discharge before recharging in order to address "memory effect" of the batteries. By fully discharging occasionally, batteries are better able to maintain the capacity for deep discharge.

Periodic discharging/recharging can assist to deter the formation of crystals which ingrain themselves in some types of batteries (e.g. nickel-cadmium) when no exercise is applied for three months or more. A full restoration with this type of periodically scheduled "exercise" becomes more difficult the longer service is withheld. In advanced cases 'reconditioning' of the battery is required (e.g., reconditioning may entail a slow, secondary discharge applied below the 1 volt/cell threshold. During this process, the current must normally be kept low to minimize cell reversal). The PRC 38/PTC 39 (or discharge/recharge module 218) can therefore be programmed to implement this periodic exercise. Further, the PRC 38/PTC 39 can be designed to shut off recharging operations when these are complete in order not to over-charge the battery. During discharging/recharging operations one battery can provide energy to the device while the other battery is undergoing this type of battery conditioning. The PRC 38, may also perform its discharging/recharging routine under control of signals sent from a power transmitter 12 (and its discharge/recharge device 268) or other device that communicates with the device 5 within which the power harvester device 60 is implemented.

Heating and Cooling

In one embodiment, the temperature modules 220,270 can use Peltier circuits to provide heating or cooling of the rechargeable power supplies 208,258 in order to alter recharging or operational performance. For example, heating a battery can momentarily increase its output by lowering the resistance. Although heating and cooling of the batteries can be used to change battery characteristics during operation, this is not commonly done since thermal regulation requires a relatively large amount of energy. However, an efficient wireless power supply can permit these types of modulation in temperature to occur since additional power can subsequently be transmitted to the rechargeable power source. In order to meet higher power operational demands, thermal regulation of the battery may be accomplished from time to time.

An implantable medical device should normally operate at approximately body temperature (e.g., 37 degrees Celsius). In one embodiment, heat modulation circuitry has an activation point that is set in a range slightly above or below 37 degrees (e.g., about 35 degrees to 43 degrees). In another embodiment the heat modulation/sensing devices only allow operation or recharging to occur as long as battery temperatures stay within a selected range. In another embodiment the heat modulation/sensing devices only allow operation or recharging of particular sets of selected batteries to occur as long as battery temperatures stay within a selected range. The device can be configured to alternate the batteries which are used in order to maintain a temperature of below a selected threshold level. The device can also be configured with a thermally active circuit which mechanically responds to excessive amounts of heat (e.g. by opening a physical contact) in order to maintain a temperature of below a selected hazard threshold limit value.

Figure 11A:
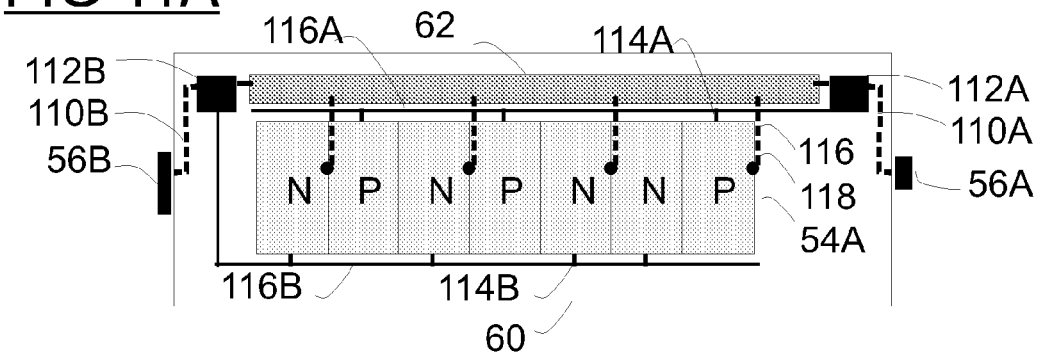
FIGS. 11A-11C illustrate wireless power-pack embodiments which address issues of recharging and temperature issues.
Figure 11B:
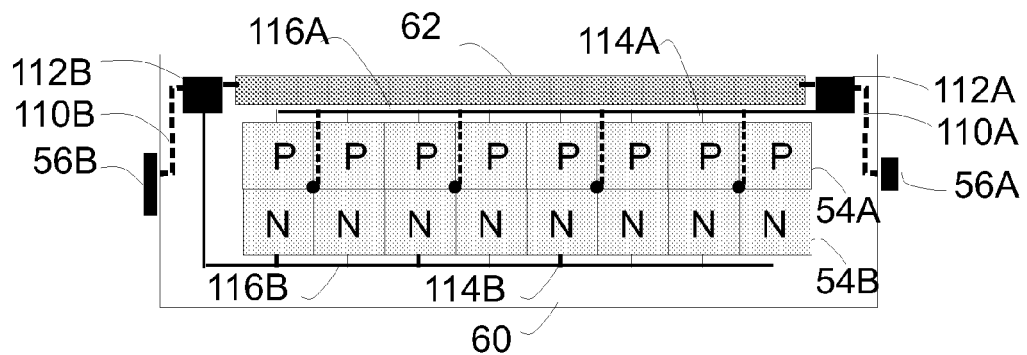
Figure 11C:
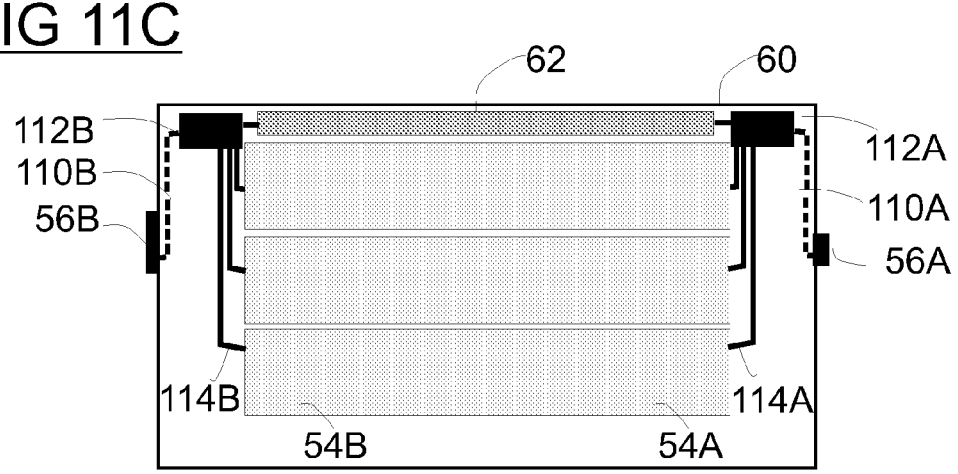

FIG. 11A illustrates a wireless power receiver device which, in this example, is configured in the form of a battery. The positive portions 54A of multiple battery elements (or elements of a single power supply) can make contact with the positive end of an energy harvester 60 through a multi-stranded positive power pathway 116A which is uniquely connected to each positive portion by way of positive power terminals 114. The positive power pathway is routed to a positive terminal control 112A which can operatively connect the positive battery elements to the positive output terminal 56A and the positive side of the wireless power harvester device. Likewise, the negative battery terminals 54A are uniquely connected to a multi-stranded negative power pathway 116B which communicates this power to the negative terminal control 112B for connection to the negative side of the power harvester module 60 and negative output terminal 56B. Thermal elements 118 can be situated between pairs of batteries and can be attached to the energy harvesting module 60 and can serve to sense temperature and also to modulate temperature. The wireless power module 62 can be configured to recharge or operate from the batteries in a manner that regulates the temperature within a selected range. Further the thermal elements 118 can modulate temperature to achieve desired features related to recharging and operation. Although embodied in a "battery-like" power-pack design, the components would like be realized in a distributed manner and would be under control of, and rely upon, a device which was being powered from the wireless power supply 62. However, if the thermal elements 118 are configured so that when these are heated they break a 'circuit' (which may be a chemically-responsive circuit-like property of fluids used in the wireless power supply, a physical property of a capacitance circuit, or which may be accomplished using various forms of MEMs technology), and halt power storage in particular cells of the battery, then implementation in something the size of a battery is possible. It should be noted that the battery elements can be configured in an alternating P-N-P manner, or can be organized as P-N-N-P in order that charging of adjacent cells biases any thermal energy towards the positive or negative elements. Other geometrical arrangements may also provide benefits. FIG. 11B shows an alternative arrangement to that of FIG. 11A and wherein many more power supply elements are used. Use of smaller elements can allow greater flexibility of temporal-spatial recharging patterns, and may serve to decrease the temperatures created during recharging or operation. FIG. 11C shows an embodiment in which at least 3 rather than 2 batteries are used in order to decrease the temperature which would occur when only two are used, since the recharging operations may be temporally—and spatially distributed.

Power Harvesting Circuit Embodiments

Figure 12A:
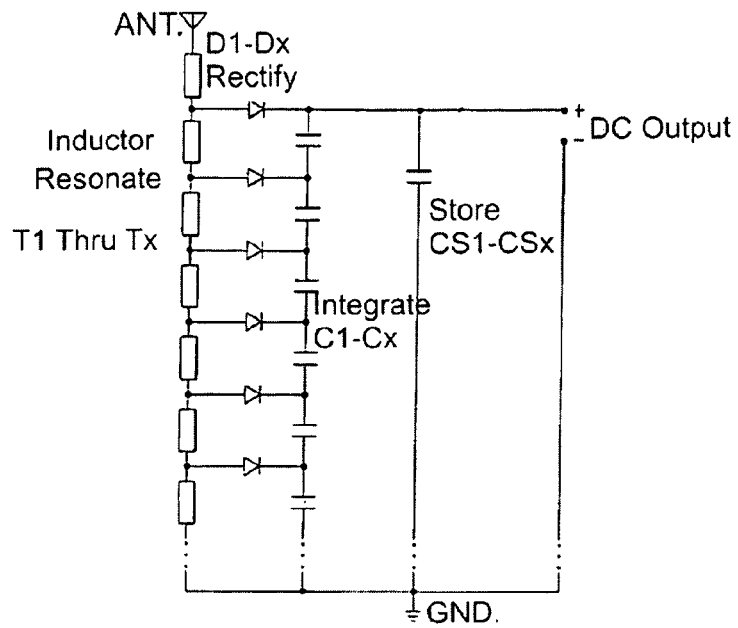
FIG. 12A-D illustrate power harvester module circuit designs to be used in wireless power-packs.

FIG. 12A shows an energy harvesting circuit as disclosed in US 2006/0164866, to Vanderelli et al. The circuit serves to convert RF energy into current using a series of taps each 'tuned' to different RF frequencies. The diodes DI-Dx, allow harnessed energy to flow in one direction only leading to charge buildup of the capacitors. While this embodiment serves well, the energy derived is related primarily to one half of the transmitted frequency that is 'captured' by the antenna.

Figure 12B:
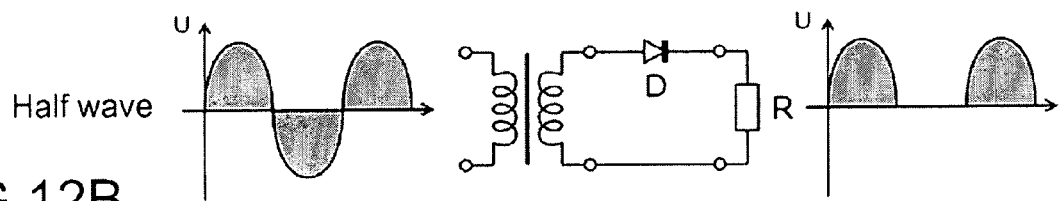
Figure 12C:
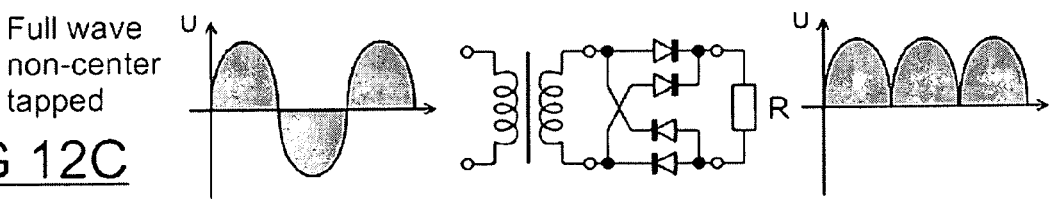
Figure 12D:
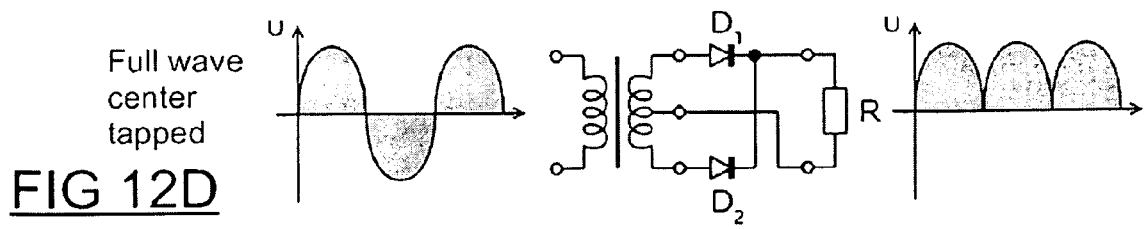

Rather than deriving current using half wave rectification, which occurs by implementing the circuit shown in FIG. 12B, a full wave rectifier (FIG. 12C) may have been implemented which would lead to harnessing of energy from both sides of the RF 'zero' line. Alternatively, the full wave rectifier shown in FIG. 12D can be used when the energy is center tapped. Further, additional types of 'polarity reversing' modules may be used.

Alternatively, the simple half wave rectifier can be built in two versions with the diode pointing in opposite directions. The first version connects the negative terminal of the output directly to the taps (here functioning as an AC supply) and the $2^{nd}$ version connects the positive terminal of the output directly to the taps. By combining both of these versions of the circuit with separate output smoothing (via capacitors) it is possible to obtain an output voltage of nearly double the peak RF (AC) input voltage. This also provides a tap in the middle which allows use of such a combined circuit to serve as a split rail supply. Alternatively, one can use two capacitors in series for the output smoothing on a bridge rectifier and then place a switch between the midpoint of those capacitors and one of the AC input terminals. With the switch open this circuit will act like a normal bridge rectifier with it closed it will act like a voltage doubling regulator. By implementing a switch within the circuit, and allowing for more than one type of rectification to occur the energy harvesting operations can be tailored either to the types of RF which are received (in order to improve energy harvesting) or to the type of power requirements of the device which is being powered, or the characteristics of the power storage supply, or both. Such a circuit may be useful, since power may be obtained from a half-wave rectifier than a full wave rectifier circuit when the signal is not centered (i.e. offset).

In addition to having fixed taps, the functional "location" or resonance of the taps may be adjusted using programmable resistors which are functionally connected to at least one portion of the antenna. This allows the taps to achieve programmable adjustment in order to allow these to harness various RF frequencies which may be ambient in the local environment, due to local or remote sources of RF transmission.

Implantable Embodiments

In addition to the embodiments shown, wireless rechargeable-power supply device 60 may include, either within a single enclosure or in a distributed fashion, modules having a battery test circuit, capacitors, battery SPDT switches as well as other types of switches. In one embodiment, the wireless rechargeable-power supply device 60 would charge a first primary battery 64A having chemistry optimized for high volume density and being able to operate the low current (<20 ma) electronics, while the secondary battery 64B would have chemistry optimized to provide high current typically >20 ma.

The primary battery could be a lithium thionel chloride battery having the high energy density which typically will maintain a low self discharge rate so long as the current drain remains below 20 ma and the secondary battery could be a LiMnO battery which can provide >50 ma current drain without affecting the battery self discharge rate. Additional batteries which are rechargeable or not can be implemented within the design. Battery designs which constitute one type of preferable embodiment for use with implanted devices are disclosed and reviewed by U.S. Pat. No. 7,127,293, to MacDonald.

In the case of an implantable power harvester the issue of transmission through tissue causes immediate obstacles since the transmitted power is greatly attenuated by tissue. In the case of a neurological device, the antenna may be located approximately extra-cranially and can communicate with one or more intracranial or skull mounted neurostimulators. In the case of an implanted cardiac device, there is not such convenient location where a relatively large antenna can be situated. One solution is to utilize the electrical conduits ('electrodes' or 'leads') which are used for sensing and stimulation in as reception antenna for power harvesting. Another is to utilize a portion of the outer shell of the device or "can" when this is conductive. If a portion of the can is used for power harvesting, then this may be electrically isolated from other parts which are used for stimulation or sensing purposes. Another alternative is to embody an antenna for power reception within the housing of the sheath through which the stimulation/sensing electrodes are fed. In another alternative embodiment, the antenna may only be situated in a first portion of the sheath which has a larger diameter. In another alternative embodiment, the at least two antenna are situated in a portion of the sheath, and each antenna and/or respective energy harvesting module which it is a part of, is tuned to receive energy that is transmitted with a specific energy profile. In another alternative embodiment, the at least two antenna are situated in a portion of the sheath, and each antenna is a part of a data or power transmission module. In another alternative embodiment, the at least two antenna are situated in a portion of the sheath, and each antenna can be programmably allocated to serve as a part of a data or power transmission module.

Miscellaneous Commercial Embodiments

Figure 13A:
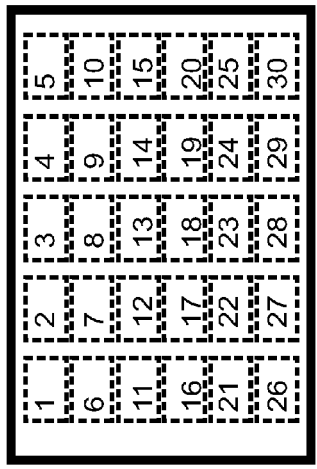
FIGS. 13A-E illustrate implementations of power pads configured for biasing and organizing devices for which the pad will serve as a wireless rechargeable power supply.

A multitude of innovative commercial embodiments for wireless power systems can be realized. The following provide several examples which can provide advantages over what has been described elsewhere:

a. Pads. Whether wireless power is provided via near or far field manner, the charging device may be realized as a charging pad (e.g. as is implemented by Splashpower and Wildcharge). When the pad charges by induction the devices can be placed on top of a grid which automatically adjusts its charge to the orientation and power needs of these devices. Alternatively, a power transmitter can be located someone on die device and can charge devices placed within the boundaries the pad (as well as beyond). In order to improve charging in either case, the pad may be provided with several features. Firstly, the pad may have a 'mapping feature' such as a numbered grid, outlines, tracings, or the like. The mapping feature may simply be graphical, or may have a physical constraints such as beveled or shaped surfaces which guide placement of devices to be charged. The mapping feature may be relevant to specified devices. In FIG. 13A, the mapping feature is realized as a numbered grid 360. When a consumer purchases a device, such as a cell phone, the device may have instructions such as: "this device may experience optimum charge by aligning the top portion between grid numbers '10' and '15' on a Splashpad or grid numbers '7' and '8' on the Wildcharge charger".

Figure 13B:
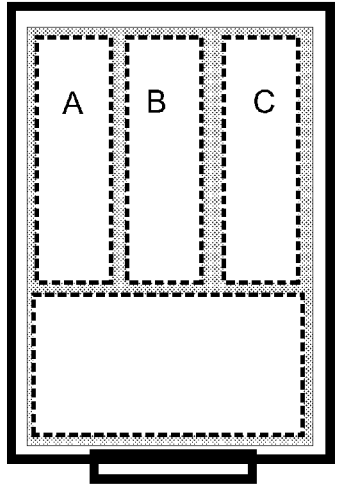
Figure 13C:
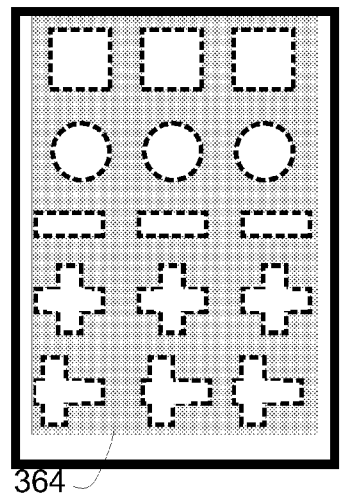
Figure 13D:
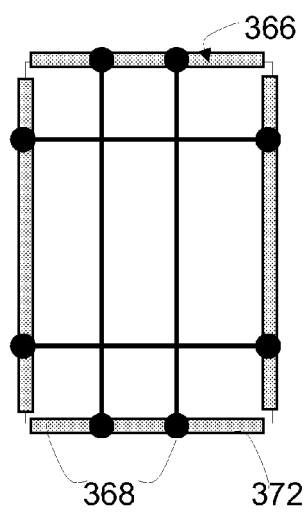
Figure 13E:
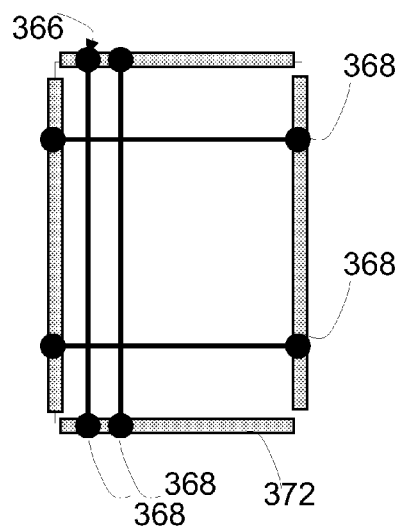

In FIG. 13B, the mapping feature is realized as a 'charging template' 362 which is embodied as a foam pad that lies on top of the charging pad and is configured for guiding several types of popular devices into correct locations (for example, compartments 'A', 'B', or 'C' are configured for charging common cell-phones, iPods (or other MP3 players), while 'D' is configured for charging PDAs or GPS type devices. The OEM's can provide 'charging templates' for their devices which can be used with various commercially available charging pads. The 'charging templates' can be designed to fit to the surface of the charging pad, or can be configured to reside within compartments (e.g. 'A') of the charging template (i.e. if the device is much smaller than compartment 'A', then the charging template can fit within 'A' and can further constrain the device to a portion of the region defined by compartment 'A'. FIG. 13C shows a 'lock-and-key based template' 364 in which devices are configured with wireless power receivers having 1 of several unique shapes, wherein the shapes are associated with particular charging paradigms such as voltage ranges or types of charging. FIG. 13D shows an 'adjustable charging template' 366 which permits flexibility in the geometry of the charging templates used for positioning of devices. In this case a series of horizontal fasteners 368 and vertical fasteners 370 cooperate with a structure 372 that is situated around the perimeter of the charging pad. By adjusting the positions of the fasteners the geometry of the charging templates can be adjusted to accommodate a large number of devices. In an alternative embodiment the fasteners may be oriented so as to permit the constraining to occur according to non-orthogonal axes which may be of arbitrary shape and orientation. FIG. 13E shows the adjustable charging template of FIG. 13D in a secondary configuration. The charging templates and compartments may be realized in a covered fashion such that the tops of devise are covered, and these covers may also shield the external environment from power leakage from the pad. In a further embodiment, if the surface of the charging pad is configured with small radius holes, then 'pins' can be inserted according to geometries which will constrain particular devices in one or more specific locations. The locations of the pins can be identified by joint provision of a numbered grid and set of coordinates for the pins which can be provided by the manufacturer. Further the 'compartments' or 'charging templates' can be configured with pins in order to reside in particular regions of the charging pad's surface.

b. Charge-sacks. Although wireless transmitters, for either inductive or RF charging, may be made portable there are occasions when it is preferable to realize a charger in the form of a flexible and lightweight charge-sack. For example, in order to increase rapid charging the signal can be made larger if it is contained within an isolated/shielded space which is not constrained by transmission guidelines for open-air transmission. The charge sack can comprise a first and second flexible surface, a power transmitter, and a power supply. The first and second flexible surfaces can have inner surfaces, at least one of which houses a power transmitter for emitting the wireless power signal and outer surfaces which are configured to deter leakage of wireless power into the surrounding environment. The power supply can be at least one of the following: a battery; a wireless power harvester device (including an inductive coupler for near-field recharging); and, a charging device which is configured with a plug for accepting either AC power from a wall socket or a DC power from a USB supply. The first and second surfaces can be partially secured by a fastener mechanism, such as a zipper, which may be operatively configured with the power transmitter so that the transmitter only transmits power, or only transmits at a particular higher power level, when the fastener is in a 'closed' position, as opposed to an 'open' position. The charge sack further contains an external display, which may simply by a red/green diode indicator which displays if charging is occurring, or, alternatively, the indicator may provide other information about the charging process. The charge-sack surfaces can be primarily comprised of transparent or translucent material, or may have regions which allow viewing of internal components. A charge-pack can also have inner surfaces which have fasteners for fastening particular devices in place in relation to a portion of the wireless transmitter. Safety, transducer, and other circuitry can be included in the charge-sack as is known for charging equipment. The charge-sack may be designed to reside within a briefcase, piece of luggage, or other article used for storage of electronic devices.

c. Charge-cases. Briefcases which are configured for wireless power transmission and reception can be known as charge-cases. Charge-cases have either transmission or reception antenna, or both, incorporated within their structures, as well as providing power harvesting modules in some instances. For example, the sides of a brief-case can be configured to hold plate-type antennae which are used to provide a large surface for power reception or transmission. The briefcase can also be figured with an AC or other type of connector which is configured for receiving power input to power a wireless transmitter device.

d. Outlet near-field chargers. Outlet near-field chargers are configured for being plugged into an AC socket and securing a rechargeable device so that it remains proximate to a power transmitter surface. When the wireless transmitter operates via induction, the securing component acts to secure the device to be charged relative to the inductive surface. The securing component can include a slot which allows a the device to be charged to be slid into the proper location for charging; a set of straps which can be adjusted via Velcro or other adjustable means or which are flexible (elastic) and which can be used to strap the device into place along the charging surface. The securing component can otherwise be configured to retain one or more devices off of the floor below the outlet. Outlet near-field chargers may also utilize a flexible charging bag which hangs from, and receives energy from, the charger and into which the devices to be charged are placed. Alternatively, a flexible surface such as a rubber pad including induction surfaces may be rolled down the wall and onto the floor, or may be connected to the outlet charger via a chord. The flexibility of the "charge bags" or "flexible pad" is important for increasing portability.

e. Vehicle lighting and accessories. The wireless power system can be implemented to provide power vehicle lighting, either directly or by way of a rechargeable battery attached to the back of each light. Vehicular lighting includes external lights such as headlights, undercarriage lights, brake-lights, side-marker lighting, fog lamps, cornering lamps, turn signal lighting, license plate lighting, accessory brake-lights for trailer-rigs, dual beam or '2-filament-based lighting', and LED-based lighting. Vehicular lighting also includes a 'centre high-mount stop' light which is used to indicate braking. Vehicular lighting also includes internal lighting such as a dome light, puddle lights, and convenience lights under the hood and in the trunk. Vehicular lighting also includes lighting which resides upon wheels which may provide either functional (e.g. these can be set to blink similar to a turn signal) or purely entertainment value. Use of wireless power for providing vehicular lighting obviates the need for running electrical wires throughout the vehicle. Two or more wireless power transmitters can transmit power to the front and back of the vehicle, and relay modules can harvest the power and re-transmit the power to localized areas of the vehicle or can route the power into localized harnesses which are used to physically provide power to nearby devices such as lighting devices. In the case of the front headlights, two different frequencies can be used to transmit power to the circuits which power the left and right lights. In a first embodiment, when a turn signal operation is initiated by the driver, a 'turn-signal protocol' is implemented by the transmission of power wherein the power of these two frequencies is temporally adjusted (stopped and started, or alternation between low and high power transmission intervals) in order to cause the light to blink until the driver's movements cause the 'turn-signal protocol' to be halted. In a second embodiment, power is continuously transmitted and data signals are also transmitted to data receiver circuitry attached to the lights in order to control the lights to blink according to the instructions sent in the data. Additionally, different power transmitters can be used to power lights for left/right sides, and front/back areas of the vehicle, such that 4 transmitters are used, one for each corner of the vehicle.

f. Price-displays. Wireless power/data transmission systems can be incorporated into price display technology such as that used in department and grocery stores. The display can be powered by wireless power in order to receive, store, and display price information, for example, using a small crystal-display panel. A central computer can be used to store current pricing. In one embodiment, since both power and data are transmitted wirelessly and are under control of the central computer, price displays for particular products are updated automatically. In this embodiment, the price displays contain RFID technology in which each price-display has a unique ID number associated with a product. This allows the central computer to send relevant information to the price displays for particular products. In an alternative embodiment, a handheld transmitter can be operationally connected to a central computer in order to receive price information and can then be manually positioned by a clerk and used to beam new prices to the displays. The handheld device can transmit data locally so that only a price-display that is very near will be altered, can designed to communicate particular information to particular RFIDs, or can be designed to use an infrared scanner for scanning a barcode of a product or a barcode associated with the price-display and then transmitting the pricing information in a wireless manner such as using RF energy, infrared energy, or the like, and the price display device can be configured to receive this wireless data. Alternatively, the handheld device can have a touch-pad for entering price information, which can be transmitted when the clerk presses a 'transmit' button. Price-displays can also contain circuitry and modules which require security codes prior to alternation of price information in order to decrease the chance of fraud or manipulation of the displayed information by non-registered users. Wireless price displays can be realized as displays which are: attached to individual products sold in a store; attached to the shelves which stock the products which are sold; and attached to terminals at the end of the isles where products are stored.

The presently described embodiments of the fraud deterrent systems and methods offer advantages over prior art. Although modifications and changes may be suggested by those skilled in the art, it is the intention of the inventor to embody within the patent warranted herein all changes and modifications as reasonably and properly come within the scope of their contribution to the art. All prior art cited, including internet address references, are incorporated by reference herein as if recited fully. The titles, headings, and subheadings provided in this specification are provided for organizational purposes only and are not meant to restrict the invention in any way, nor to limit material described in one section from applying to another section as would be apparent to those skilled in the art.

Although certain methods, apparatus, and articles of manufacture have been described herein, the scope of coverage of this patent is not limited thereto. To the contrary, this patent covers all methods, apparatus, and articles of manufacture fairly falling within the scope of the appended claims either literally or under the doctrine of equivalents. The preferred features of the invention are applicable to all aspects of the invention and may be used in any possible combination. Throughout the description and claims of this specification, the words "comprise" and "contain" and variations of the words, for example "comprising" and "comprises", mean "including but not limited to", and are not intended to (and do not) exclude other components, integers, additives or steps. The term 'antenna' can refer to multiple 'antennae' and can refer to a 'rectenna'. While the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

The following is claimed:

1. A rechargeable battery system for receiving wireless power comprising:
   an antenna for receiving wireless energy;
   a harvesting module for converting wireless energy into power;
   an energy storage module configured for recharging at least a first rechargeable battery while simultaneously providing power to a device from a second battery; and,
   a power receiver control module for controlling said recharging and providing power operations, said power receiver control module being implemented partially within a rechargeable battery and also being configured for making electrical connection with said device.

2. A rechargeable battery system of claim 1 wherein said power receiver control module is at least partially under control of the device.

3. A rechargeable battery system of claim 1 wherein said power receiver control module is configured to provide the device with an indication of at least one of: power level of at least one of the said batteries; amount of power being harnessed over a current period.

4. A rechargeable battery system of claim 1 further comprising an energy profile module configured to provide an indication of how much energy is available for harvesting within at least one selected spectral range.

5. A rechargeable battery system of claim 1 further comprising an energy profile module configured to provide an indication of how much energy is being harvested from at least one selected spectral range.

6. A rechargeable battery system 5 wherein said energy profile module is connected to the antenna.

7. A rechargeable battery system of claim 5 wherein said energy profile module is connected to an output of the energy harvesting module.

8. A rechargeable battery system of claim 5 wherein said recharging at least one rechargeable battery comprises recharging at least two rechargeable batteries at different moments in time.

9. A rechargeable battery system of claim 5 wherein said recharging at least one rechargeable battery comprises periodically alternating between recharging at least one of at least two rechargeable batteries at different moments in time.

10. A rechargeable battery system for receiving wireless power comprising:
   at least one wireless rechargeable battery configured with at least one recharging connection surface configured for receiving power from a wireless-power harvesting device and for storing said power, said recharging connection surface being physically distinct from terminals used for communicating power from the battery to a device; and,
   a wireless-power harvesting device configured for sending power to the recharging connection surface of the rechargeable battery.

11. The rechargeable battery system of claim 10 wherein the at least one recharging connection surface comprises a first recharging connection surface electrically coupled to a positive portion of the rechargeable battery and a second recharging connection surface electrically coupled to a negative portion of the rechargeable battery.

12. The rechargeable battery system of claim 10 wherein the wireless power harvesting device is configured for producing harvested power from a near field induction-based power transmitter and for relaying this power to the recharging connection surface of the battery.

13. The rechargeable battery system of claim 10 wherein the wireless power harvesting device is configured for producing harvested power from a far field induction-based power transmitter and for relaying said harvested power to the recharging connection surface of the battery.

14. The rechargeable battery system of claim 10 wherein the system is further configured with control circuitry for causing recharging to be controlled by commands sent from the wireless-power harvesting device.

15. The rechargeable battery system of claim 10 wherein the rechargeable battery is further configured for communication with the wireless-power harvesting device.

* * * * *